US006376539B1

(12) United States Patent
Stolle et al.

(10) Patent No.: US 6,376,539 B1
(45) Date of Patent: Apr. 23, 2002

(54) SUBSTITUTED BICYCLIC LACTONES

(75) Inventors: Andreas Stolle, Milford, CT (US); Horst-Peter Antonicek, Bergisch Gladbach (DE); Stephen Lensky, Kürten (DE); Arnd Voerste, Köln (DE); Thomas Müller, Bonn-Beuel (DE); Jörg Baumgarten, Wuppertal (DE); Karsten von dem Bruch; Gerhard Müller, both of Leverkusen (DE); Udo Stropp, Haan (DE); Ervin Horváth, Leverkusen (DE); Jean-Marie-Viktor de Vry, Rösrath (DE); Rudy Schreiber, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/600,395

(22) PCT Filed: Jan. 7, 1999

(86) PCT No.: PCT/EP99/00031

§ 371 Date: Jul. 14, 2000

§ 102(e) Date: Jul. 14, 2000

(87) PCT Pub. No.: WO99/36418

PCT Pub. Date: Jul. 22, 1999

(30) Foreign Application Priority Data

Jan. 17, 1998 (DE) .......................................... 198 01 636

(51) Int. Cl.$^7$ ....................... A61K 31/34; A61K 31/335

(52) U.S. Cl. ....................... 514/470; 514/444; 514/462; 549/60; 549/229; 549/295; 549/297; 549/302; 549/304; 549/305

(58) Field of Search .......................... 549/295, 60, 229, 549/302, 304, 305, 297; 514/444, 462, 470

(56) References Cited

U.S. PATENT DOCUMENTS 5,688,826 A 11/1997 Massey et al. .............. 514/433
5,843,988 A 12/1998 Annoura et al. ............ 514/454

FOREIGN PATENT DOCUMENTS

EP 0656345 6/1995 ......... C07C/229/36
EP 0658539 6/1995 ......... C07C/229/24

(List continued on next page.)

OTHER PUBLICATIONS

Chavis, P., Shinozaki, H., Bockaert, J., and Fagni, L., "The Metabotropic Glutamate Receptor Types 2/3 Inhibit L–Type Calcium Channels via a Pertussis Toxin–Sensitive G–Protein in Cultured Cerebellar Granule Cells", J. Neuroscience, 14(11): 7067–7076 (Nov. 1994).

Chavis, P., Nooney, J.M., Bockaert, J., Fagni, L, Feltz, A., and Bossu, J.L., "Facilitatory Coupling between a Glutamate Metabotropic Receptor and Dihydropyridine–Sensitive Calcium Channels in Cultured Cerebellar Granule Cells", J. Neuroscience, 15(1): 135–143 (Jan. 1995).

Conn, P.J., and Pin J.–P., "Pharmacology and Functions of Metabotropic Glutamate Receptors", Annu. Rev. Pharmacol. Toxicol., 37:205–237 (1997).

Armarego, W.L.F., "Quinazolines. Part XVI. A Stereospecific cis–Addition of the Elements of Nitromethane Across a Tetrasubstituted Ethylenic Double Bond", J. Chem. Soc. C, pp. 1812–1817 (1971).

Bloomfield, J.J.; Lee, S.L., "Control of Lithium Aluminum Hydride Reduction of Cyclic Dicarboxylic Acid Anhydrides to Produce γ–Lactones or Diols", J. Org. Chem. 32(12): 3919–3924 (1967).

Clive, D.L.J.; Manning, H. W.; Boivin, T.L., "Construction of trans–Ring–fused Compounds by Radical Cyclization", J. Chem. Soc. Chem. Commun., pp. 972–974 (1990).

Clive, D.L.J.; Manning, H. W.; Boivin, T. L. B.; Postema, M. H. D., "Formation of trans Ring–Fused Compounds by an Alkylation–Radical Cyclization Sequence" , J. Org. Chem. 58:6857–6873 (1993).

Dostal, C.; Lauritz, S.; Urban, E., "Synthesis and Rearrangement of Aminoalkyl Lactones to Spirocyclic Hydroxymethyl Lactams", Heteroclycles 34(1): 135–148 (1992).

Doyle, M. P.; Zhou, Q.–L., "Enantioselective Catalytic Intramolecular Cyclopropanation of Allylic α–Diazopropionates Optimized with Dirhodium(II) Tetrakis[Methyl 2–Oxazolidinone–4(S or R)–Carboxylate]", Tetrahedron: Asymmetry 6(9): 2157–2160 (1995).

Ernst, A.B.;Fristad, W.E., "Intramolecular Lactone Annulation of Activated Acids with Mn(III)", Tetrahedron Letters 26(32): 3761–3764 (1985).

Ghosh, S.; Raychaudhuri, S.R.; Salomon, R. G., "Synthesis of Cyclobutated Butyrolactones Via Copper(I)–Catalyzed Intermolecular Photocycloadditions of Homoallyl Vinyl or Diallyl Ethers", J. Org. Chem. 52: 83–90 (1987).

Hong, F.–T.;Paquette, L.A., "Efficient Stereocontrolled Synthesis of the ABC Subunit of Dumsin", Tetrahedron Letters 35(49): 9153–9156 (1994).

Ito, Y.; Kato, H.; Saegusa, T., "A New Approach for Stereoselective Synthesis of γ–Butyrolactones", J. Org. Chem. 47: 741–743 (1982).

Julia, M.;Salard, J.M.; Chottard, J. C., "Radical Cyclization. XIX. Decarboxylating Cyclization of Heptenoic Acid Hemiesters", Bull. Soc. Chim. Fr., No. 7–8, pp. 2478–2482 (1973).

(List continued on next page.)

Primary Examiner—Amelia Owens
(74) Attorney, Agent, or Firm—Jerrie L. Chiu

(57) ABSTRACT

The present invention relates to novel substituted bicyclic lactones, to processes for their preparation and to their use for the prevention and/or treatment of disorders caused by hyper- or hypofunction of the glutamatergic system, in particular of cerebral ischaemias, cranial cerebral trauma, states of pain or CNS-mediated spasms.

11 Claims, No Drawings

FOREIGN PATENT DOCUMENTS

| | | | |
|---|---|---|---|
| EP | 0774454 | 5/1997 | ......... C07C/229/50 |
| EP | 0774461 | 5/1997 | |
| JP | 49110659 | 10/1974 | |
| WO | 9210583 | 6/1992 | ........... C12P/21/06 |
| WO | 9515940 | 6/1995 | ......... C07C/229/24 |
| WO | 9515941 | 6/1995 | ......... C07C/229/36 |
| WO | 9525110 | 9/1995 | ......... C07D/513/04 |
| WO | 9605818 | 2/1996 | ......... A61K/31/135 |
| WO | 9607405 | 3/1996 | |
| WO | 9615099 | 5/1996 | |
| WO | 9615100 | 5/1996 | ......... C07C/229/46 |
| WO | 9701790 | 1/1997 | ......... G02F/1/1337 |
| WO | 9705109 | 2/1997 | ......... C07D/209/18 |
| WO | 9705137 | 2/1997 | ......... C07D/473/04 |

OTHER PUBLICATIONS

Kayser, M. M.; Salvador, J.; Morand, P., "Metal Hydride Reductions of Unsymmetrically Substituted Cyclic Anhydrides Attached to Strained Ring Systems", Can. J. Chem. 60:1199–1206.

Krafft, M.E.; Chirico, X., "Synthesis of a Model for the Xestobergsterol D and E Rings Using the Pauson–Khand Reaction", Tetrahedron Letters 35(26): 4511–4514 (1994).

Lee, G.M.; Parvez, M.; Weinreb, S. M., "Intramolecular Metal Catalyzed Kharasch Cyclizations of Olefinic α–Halo Esters and Acids", Tetrahedron 44(15):4671–4678 (1988).

Mori, K., Miyake, M., "Pheromone Synthesis. 100. A New Synthesis of Both the Enantiomers of Grandisol, the Boll Weevil Pheromone", Tetrahedron 43(10):2229–2239 (1987).

Paquette, L. A.; Gardlik, J. M.; McCullough, K. J.; Hanzawa, Y., "Bond Fixation in Annulenes. 15. A Titanium(0)–Mediated Synthesis of a Cyclooctatetraene. Probe of the Relative Size of the Interstitial Phenyl Substituent in 1,3–Dimethyl–2–phenylcyclooctatetraene by Means of Racemization Kinetics", J.Am.Chem.Soc. 105: 7644–7648 (1983).

Raychaudhuri, S. R.; Ghosh, S.; Salomon,R. G., "Copper(I-)Catalysis of Olefin Photoreactions. 11. Synthesis ofMulticyclic Furans and Butyrolactones Via Photobicyclization of Homoallyl Vinyl and Diallyl Ethers", J.Am. Chem. Soc. 104: 6841–6842 (1982).

Shimada, M.; Kovayashi, S.; Ohno, M., "Efficient Stereocontrol of a Quaternary Chiral Center in the Cyclohexene Systems. Potential Chiral Synthons for Vitamin D and Related Compounds by Enzymatic Approach", Tetrahedron Letters 29(52): 6961–6964 (1988).

Smith, A. B. III; Visnick, M., "An Expedient Synthesis of Substituted Indoles", Tetrahedron Letters 26(32): 3757–3760 (1985).

Stejskal,R.;Urban, E.; Völlenkle, H., "Synthesis and Determination of Configuration of Potential Antimicrobial 5,6–Dihydroxyisobenzofuranones", Monatsh. Chem. 122(3): 145–156 (1991).

Trost, B.M.; Miller, C. H., "New Synthetic Methods. A Ring Expansion Approach to α–Methylene δ–Lactones", J. Am. Chem. Soc. 97(24): 7182–7183 (1975).

SUBSTITUTED BICYCLIC LACTONES

The present invention relates to substituted bicyclic lactones, to processes for their preparation and to their use as pharmaceuticals.

The amino acid L-glutamate is the most important excitatory neurotransmitter in the brain. Glutamate receptors can be divided into two major classes: 1. ionotropic receptors which control ion channels directly and 2. metabotropic receptors (mGluRs).

Metabotropic glutamate receptors are a heterogeneous class of G-protein-coupled receptors. Pre- and postsynaptically, they modulate the release of glutamate and the sensitivity of the cell to glutamate, respectively. The effects are caused via different second-messenger cascades. This response, in turn, has an effect on the ionotropic glutamate receptors.

Presently, 8 different subtypes of metabotropic glutamate receptors are known, differing in the second-messenger cascade, pharmacology and localization in the brain (review in: Ann. Rev. Pharmacol. Toxicol. 1997, 37, 205).

The present invention relates to substituted bicyclic lactones of the general formula (I)

(I)

in which

A represents radicals of the formulae —$CH_2$—, —CO—, —$CR^4(OH)$— or —$(CH_2)_a$—$CHR^5$—, in which a represents a number 0, 1, 2, 3 or 4, $R^4$ represents hydrogen or ($C_1$–$C_6$)-alkyl and $R^5$ represents phenyl, or represents ($C_2$–$C_8$)-alkanediyl, ($C_2$–$C_6$)-alkenediyl or ($C_2$–$C_6$)-alkinediyl, $R^1$ represents hydrogen, ($C_3$–$C_6$)-cycloalkyl or represents a 5- to 6-membered heterocycle which may contain up to 3 hetero-atoms from the group consisting of S, O and N and/or a radical of the formula —$NR^6$, in which $R^6$ represents hydrogen or methyl, or represents a 5- to 6-membered benzo-fused heterocycle which may contain up to 2 heteroatoms from the group consisting of S, O and N and/or a radical of the formula —$NR^7$, and which may be attached both via the phenyl ring and via the heterocycle, in which $R^7$ has the meaning of $R^6$ given above and is identical to or different from this meaning, or represents radicals of the formulae in which b and c are identical or different and represent a number 1 or 2, or represents ($C_6$–$C_{10}$)-aryl, where all of the ring systems listed above are optionally mono- to polysubstituted by identical or different substituents selected from the group consisting of halogen, cyano, nitro, trifluoromethyl, hydroxyl, ($C_1$–$C_6$)-alkoxy and ($C_3$–$C_6$)-cycloalkyl, phenyl, phenoxy, benzyloxy and a 5- to 6-membered aromatic heterocycle having up to 3 heteroatoms from the group consisting of S, N and/or O, which for their part may be substituted up to three times by identical or different substituents from the group consisting of cyano and halogen, and/or are substituted by ($C_1$–$C_6$)-alkyl and ($C_2$–$C_6$)-alkylene, which for their part may be substituted by halogen, ($C_6$–$C_{10}$)-aryl or by radicals of the formula —$SR^8$, —$OR^9$ or —$NR^{10}R^{11}$ or in which $R^8$ represents ($C_1$–$C_6$)-alkyl or phenyl, $R^9$ represents hydrogen or ($C_1$–$C_6$)-alkyl, and $R^{10}$ and $R^{11}$ are identical or different and represent hydrogen, phenyl or ($C_1$–$C_6$)-alkyl, which is optionally substituted by phenyl, which for its part may be mono- to polysubstituted by identical or different substituents from the group consisting of halogen, nitro, hydroxyl and ($C_1$–$C_6$)-alkoxy, or $R^{10}$ and $R^{11}$ together with the nitrogen atom form a radical of the formula in which G represents an oxygen atom, a —$CH_2$ group or a radical of the formula —$NR^{12}$—, in which $R^{12}$ represents hydrogen, phenyl, benzyl, $(C_1-C_6)$-alkyl, $(C_1-C_6)$-alkoxy-carbonyl or a 5- to 6-membered aromatic heterocycle having up to 3 heteroatoms from the group consisting of S, N and/or O, and/or are substituted by groups of the formulae $-CO_2-R^{13}$, $-NR^{14}R^{15}$, $-NR^{16}CO-R^{17}$, $-NR^{18}CO_2-R^{19}$ and $-CO-NR^{20}R^{21}$, in which $R^{13}$ represents hydrogen, or represents $(C_1-C_9)$-alkyl or $(C_2-C_6)$-alkenyl, which for their part may be substituted by radicals of the formulae

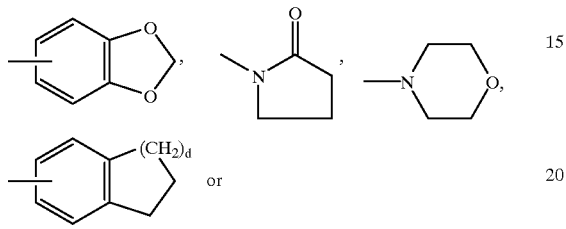

$(C_6-C_{10})$-aryl or by a 5- to 7-membered aromatic heterocycle having up to 3 heteroatoms from the group consisting of S, N and/or O, in which d represents a number 1 or 2, or represents $(C_6-C_{10})$-aryl, which is optionally substituted by phenyl, which for its part may be substituted by cyano or halogen, $R^{14}$ and $R^{15}$ are identical or different and represent hydrogen, $(C_3-C_6)$-cycloalkyl, phenyl or $(C_1-C_6)$-alkyl, which is optionally substituted by $(C_3-C_6)$-cycloalkyl or phenyl, which for its part may be mono- to polysubstituted by identical or different substituents from the group consisting of halogen, hydroxyl or $(C_1-C_6)$-alkoxy, $R^{16}$ represents hydrogen or $(C_1-C_6)$-alkyl, $R^{17}$ represents hydrogen, adamantyl, $(C_3-C_8)$-cycloalkyl, $(C_2-C_6)$-alkenyl or $(C_1-C_{12})$-alkyl which is optionally substituted by adamantyl, $(C_3-C_6)$-cycloalkyl, $(C_6-C_{10})$-aryl, phenoxy or a 5-to 6-membered aromatic heterocycle having up to 3 hetero-atoms from the group consisting of S, N and/or O, where aryl and the heterocycle for their part may be mono- to polysubstituted by identical or different substituents from the group consisting of $(C_1-C_6)$-alkyl, $(C_1-C_6)$-alkoxy, hydroxyl, nitro or halogen, and/or alkyl is optionally substituted by a radical of the formula

in which e represents a number 0 or 1 and $R^{22}$ represents $(C_1-C_6)$-alkyl or $(C_6-C_{10})$-aryl, which is optionally mono- to polysubstituted by identical or different substituents from the group consisting of halogen, nitro, hydroxyl and $(C_1-C_6)$-alkoxy, or represents $(C_6-C_{10})$-aryl or a 5- to 6-membered aromatic heterocycle having up to 3 heteroatoms from the group consisting of S, N and/or O, which for their part may optionally be mono- to polysubstituted by identical or different substituents from the group consisting of $(C_1-C_6)$-alkoxy, $(C_1-C_6)$-alkyl, hydroxyl, nitro and halogen, or represents a radical of the formula

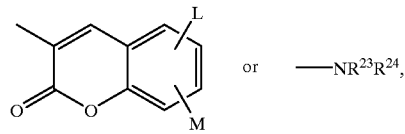 or $-NR^{23}R^{24}$, in which

L and M are identical or different and represent hydrogen or halogen, $R^{23}$ and $R^{24}$ have the meaning of $R^{10}$ and $R^{11}$ given above and are identical to or different from this meaning, $R^{18}$ has the meaning of $R^{16}$ given above and is identical to or different from this meaning, $R^{19}$ represents $(C_3-C_8)$-cycloalkyl, or represents $(C_1-C_8)$-alkyl or $(C_2-C_8)$-alkenyl, which for their part are optionally substituted by substituents selected from the group consisting of halogen, phenyl, hydroxyl, morpholinyl, $(C_3-C_8)$-cycloalkyl and by a group of the formula $-SiR^{25}R^{26}R^{27}$, in which $R^{25}$, $R^{26}$ and $R^{27}$ are identical or different and represent $(C_1-C_6)$-alkyl, $R^{20}$ and $R^{21}$ are identical or different and represent hydrogen, adamantyl, $(C_3-C_8)$-cycloalkyl, phenyl, phenoxy-substituted phenyl or a 5- to 6-membered, aromatic heterocycle having up to 3 heteroatoms from the group consisting of S, N and/or O, or represent $(C_2-C_8)$-alkenyl, $(C_1-C_{12})$-alkyl or $(C_2-C_6)$-alkinyl, which are optionally substituted by hydroxyl, $(C_3-C_6)$-cycloalkyl, $(C_1-C_6)$-alkoxy, halogen, hydroxyl, trifluoromethyl, phenyl or by a 5- to 6-membered aromatic heterocycle having up to 3 heteroatoms from the group consisting of S, N and/or O, where the ring systems are optionally substituted up to 2 times by identical or different substituents from the group consisting of $(C_1-C_6)$-alkoxy, $(C_1-C_6)$-alkoxycarbonyl, halogen, phenoxy, hydroxyl and $(C_1-C_6)$-alkyl, and/or the alkyl listed under $R^{20}/R^{21}$ is optionally substituted by radicals of the formulae

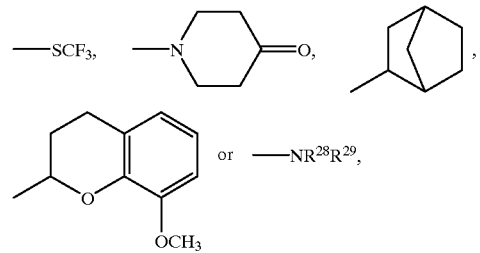

in which $R^{28}$ and $R^{29}$ are identical or different and represent hydrogen or $(C_1-C_6)$-alkyl, or represents a radical of the formula

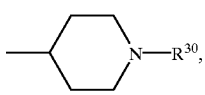

in which $R^{30}$ has the meaning of $R^{12}$ given above and is identical to or different from this meaning, or $R^{20}$ and $R^{21}$ together with the nitrogen atom form a radical of the formula

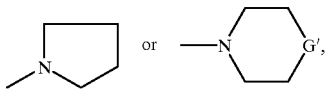

in which

G' has the meaning of G given above and is identical to or different from this meaning, $R^2$ and $R^3$ are identical or different and represent hydrogen or $(C_1-C_6)$-alkyl, and D and E together represent radicals of the formulae

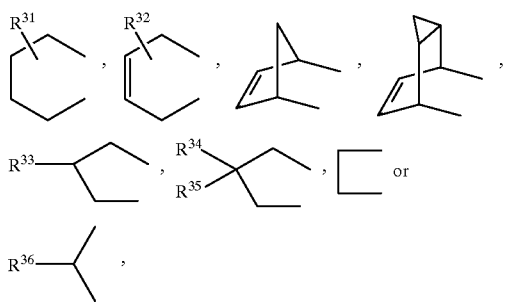

in which $R^{31}$ and $R^{32}$ are identical or different represent hydrogen or $(C_1-C_6)$-alkyl, $R^{33}$ represents hydrogen, hydroxyl, $(C_1-C_6)$-alkoxy, $(C_1-C_6)$-alkoxycarbonyl, carboxyl or $(C_1-C_6)$-alkyl, which is optionally substituted by hydroxyl, carboxyl or $(C_1-C_6)$-alkoxycarbonyl, or represents a radical of the formula $—OR^{37}$, in which $R^{37}$ represents $(C_1-C_6)$-alkenyl or $(C_1-C_6)$-alkyl, which is optionally substituted by $(C_3-C_8)$-cycloalkyl or $(C_6-C_{10})$-aryl, which for its part is substituted by halogen, nitro, trifluoromethyl or $(C_1-C_6)$-alkyl, or represents a radical of the formula $—SO_2R^{38}$, in which $R^{38}$ represents $(C_6-C_{10})$-aryl or $(C_1-C_6)$-alkyl, $R^{34}$ and $R^{35}$ are identical or different and represent halogen, hydroxyl, carboxyl, $(C_1-C_6)$-acyloxy or amino, or represent $(C_1-C_6)$-alkyl, which is optionally substituted by hydroxyl or $(C, -C_6)$-acyloxy, or $R^{34}$ and $R^{35}$ together with the adjacent ring carbon atom form a radical of the formula

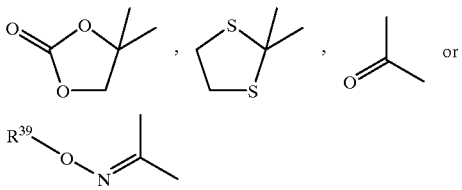

in which $R^{39}$ represents hydrogen or $(C_1-C_4)$-alkyl, and $R^{36}$ represents $(C_1-C_6)$-alkoxycarbonyl, or represents $(C_1-C_6)$-alkyl, which is optionally substituted up to 2 times by identical or different substituents from the group consisting of hydroxyl, $(C_1-C_6)$-alkoxy and $(C_1-C_6)$-alkoxycarbonyl, and their pharmaceutically acceptable salts.

The compounds according to the invention can exist in stereoisomeric forms which either behave as image and mirror image (enantiomers), or which do not behave as image and mirror image (diastereomers). The invention relates both to the enantiomers or diastereomers and their respective mixtures. Like the diastereomers, the racemic forms can be separated into the stereochemically uniform components in a known manner.

Physiologically acceptable salts of the compounds according to the invention can be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, mateic acid or benzoic acid.

Salts which can be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldulsopropylamine, procaine, dibenzylamine, N-methylmorpholine, dihydroabietylamine, 1-ephenamine or methylpiperidine.

In the context of the invention, $(C_3-C_8)$-cycloalkyl and $(C_3-C_6$-cycloalkyl represent cyclopropyl, cyclopentyl, cyclobutyl, cyclohexyl, cycloheptyl or cyclooctyl. Preferred examples which may be mentioned are: cyclopropyl, cyclopentyl, cyclohexyl or cycloheptyl.

In general, $(C_6-C_{10})$-aryl represents an aromatic radical having 6 to 10 carbon atoms. Preferred aryl radicals are phenyl and naphthyl.

In the context of the invention, $(C_1-C_{10})$-alkyl, $(C_1-C_9)$-alkyl, $(C_1-C_8)$-alkyl and $(C_1-C_6)$-alkyl represent a straight-chain or branched alkyl radical having 1 to 12, 1 to 9, 1 to 8 and 1 to 6 carbon atoms, respectively. Preference is given to a straight-chain or branched alkyl radical having 1 to 6 carbon atoms. Examples which may be mentioned are: methyl, ethyl, n-propyl, isopropyl, t-butyl, n-pentyl and n-hexyl.

In the context of the invention, $(C_2-C_8)$-alkanediyl represents a straight-chain or branched alkanediyl radical having 2 to 8 carbon atoms. Preference is given to a straight-chain or branched alkanediyl radical having 2 to 6 carbon atoms, particularly preferably 2 to 4 carbon atoms. Examples which may be mentioned are ethylene, propylene, propane-1,2-diyl, propane-2,2-diyl, butane-1,3-diyl, butane-2,4-diyl, pentane-2,4-diyl, 2-methyl-pentane-2,4-diyl.

In the context of the invention, $(C_2–C_6)$-alkenediyl represents a straight-chain or branched alkenediyl radical having 2 to 6 carbon atoms, preferably 2 to 4 carbon atoms, particularly preferably 3 carbon atoms. Examples which may be mentioned are ethene-1,2-diyl, ethene-1,1-diyl, propene-1,1-diyl, propene-1,2-diyl, propene-1,3-diyl, propene-3,3-diyl, propene-2,3-diyl, but-2-ene-1,4-diyl, pent-2-ene-1,4-diyl, hex-2-ene-1,4-diyl.

In the context of the invention, $(C_2–C_6)$-alkinediyl represents a straight-chain or branched alkinediyl radical having 2 to 6 carbon atoms, preferably 2 to 4 carbon atoms, particularly preferably 2 to 3 carbon atoms. Examples which may be mentioned are ethine-1,2-diyl, propine-1,3-diyl, but-2-ine-1,4-diyl, pent-2-ine-1,4-diyl, hex-2-ine-1,4-diyl.

In the context of the invention, $(C_1–C_6)$-alkoxy represents a straight-chain or branched alkoxy radical having 1 to 6 carbon atoms. Preference is given to a straight-chain or branched alkoxy radical having 1 to 4 carbon atoms. Examples which may be mentioned are: methoxy, ethoxy, n-propoxy, isopropoxy, t-butoxy, n-pentoxy and n-hexoxy.

In the context of the invention, $(C_1–C_6)$-alkoxycarbonyl represents a straight-chain or branched alkoxycarbonyl radical having 1 to 6 carbon atoms. Preference is given to a straight-chain or branched alkoxycarbonyl radical having 1 to 4 carbon atoms. Examples which may be mentioned are: methoxycarbonyl, ethoxycarbonyl, n-propoxycarbonyl, iso-propoxycarbonyl and t-butoxycarbonyl.

In the context of the invention, $(C_2–C_8)$-alkenyl and $(C_2–C_6)$-alkenyl represent a straight-chain or branched alkenyl radical having 2 to 8 carbon atoms and 2 to 6 carbon atoms, respectively. Preference is given to a straight-chain or branched alkenyl radical having 2 to 4 carbon atoms. Examples which may be mentioned are: vinyl, allyl, isopropenyl and n-but-2-en-1-yl.

In the context of the invention, $(C_2–C_6)$-alkinyl represents a straight-chain or branched alkinyl radical having 2 to 6 carbon atoms. Preference is given to a straight-chain or branched alkinyl radical having 2 to 4 carbon atoms. Examples which may be mentioned are: ethenyl, n-prop-2-in-1-yl and n-but-2-in-1-yl.

In the context of the invention, a 5- to 6-membered heterocycle generally represents a 5- to 6-membered, optionally also aromatic, heterocycle which may contain up to 3 heteroatoms from the group consisting of S, O and/or N or a radical of the formula —NH or —NCH$_3$. Examples which may be mentioned are: pyridyl, pyrimidyl, pyridazinyl, thienyl, furyl, pyrrolyl, thiazolyl, oxazolyl, imidazolyl, piperidinyl or morpholinyl. Preference is given to pyridyl, pyrimidyl, pyridazinyl, furyl and thiazolyl.

In the context of the invention, a 5- to 6-membered, benzo-fused heterocycle generally represents a 5- to 6-membered, preferably 5-membered heterocycle having up to 2 heteroatoms from the group consisting of S, O, N and/or a radical of formula —NH, whose ring carbon atoms are the attachment points for the benzene ring. Examples which may be mentioned are: indolyl, benzimidazolyl, benzothiophenyl, benzofuranyl, benzoxazolyl, quinolyl, quinoxalinyl or quinazolyl. Preference is given to benzimidazolyl, quinolyl, quinoxalinyl, quinazolyl, benzothiophenyl and benzofuranyl.

Preference is given to compounds of the general formula (I) according to the invention, in which A represents radicals of the formulae —CH$_2$—, —CO—, —CR$^4$(OH)— or —(CH$_2$)$_a$ — CHR$^5$—,
  in which
  a represents a number 0, 1, 2 or 3.
  R represents hydrogen or $(C_1–C_4)$-alkyl, and R$^5$ represents phenyl, or
  represents $(C_2–C_6)$-alkanediyl, $(C_2–C_4)$-alkenediyl or $(C_2–C_4)$-alkinediyl, R$^1$ represents hydrogen, cyclopropyl, cyclopentyl or cyclohexyl, or represents benzofuranyl, benzothiophenyl, benzimidazolyl, thienyl, furyl, quinazolyl, quinoxalinyl or quinolyl, or
  represents radicals of the formulae

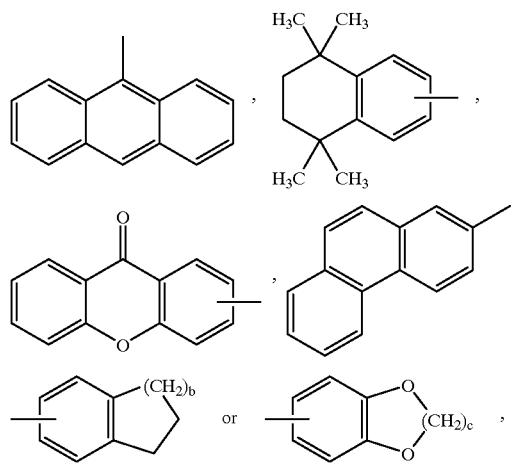

in which
b and c are identical or different and represent a number 1 or 2, or represents phenyl or naphthyl,
where all of the ring systems listed above may optionally be mono- to polysubstituted by identical or different substituents selected from the group consisting of fluorine, chlorine, bromine, iodine, cyano, nitro, trifluoromethyl, hydroxyl or $(C_1–C_5)$-alkoxy, cyclopropyl, cyclopentyl, cyclohexyl, phenyl, phenoxy, pyridyl, pyrimidyl, pyridazinyl, thienyl, furyl or benzyloxy, which for their part may be substituted up to three times by identical or different substituents from the group consisting of cyano, fluorine, chlorine, bromine and iodine, and/or are substituted by $(C_1–C_5)$-alkyl and $(C_2–C_4)$-alkenyl, which for their part may be substituted by fluorine, chlorine, bromine, iodine, phenyl, naphthyl or by radicals of the formula —SR$^8$, —OR$^9$ or —NR$^{10}$R$^{11}$ or

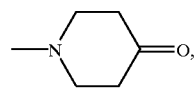

in which
R$^8$ represents $(C_1–C_4)$-alkyl or phenyl,
R$^9$ represents hydrogen or $(C_1–C_4)$-alkyl, and
R$^{10}$ and R$^{11}$ are identical or different and represent hydrogen, phenyl or $(C_1–C_4)$-alkyl, which is optionally substituted by phenyl, which for its part may be mono- to polysubstituted by identical or different substituents from the group consisting of fluorine, chlorine, bromine, nitro, hydroxyl and $(C_1–C_4)$-alkoxy, or $R^{10}$ and $R^{11}$ together with the nitrogen atom form a radical of the formula

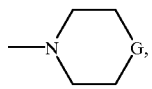

in which
G represents an oxygen atom, a —CH$_2$— group or a radical of the formula —NR$^{12}$—,
in which
$R^{12}$ represents hydrogen, phenyl, benzyl, (C$_1$–C$_4$)-alkyl, (C$_1$–C$_4$)-alkoxycarbonyl, pyridyl, pyrimidyl, pyridazinyl or furyl,
and/or are substituted by groups of the formula —CO$_2$—R$^{13}$, —NR$^{14}$R$^{15}$, —NR$^{16}$CO—R$^{17}$, —NR$^{18}$CO$_2$—R$^{19}$ and —CO—NR$^{20}$R$^{21}$,
in which
$R^{13}$ represents hydrogen, or represents (C$_1$–C$_8$)-alkyl or (C$_2$–C$_5$)-alkenyl, which for their part may be substituted by radicals of the formulae

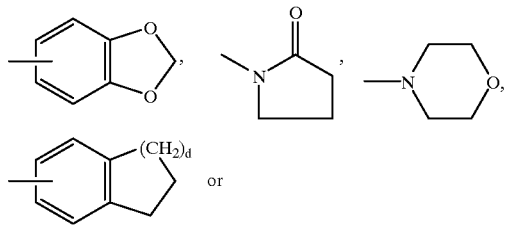

phenyl, naphthyl, pyridyl ievt orfuI
in which
d represents a number 1 or 2, or
represents phenyl or naphthyl, which are optionally substituted by phenyl, which for its part may be substituted by cyano, fluorine, chlorine or bromine,
$R^{14}$ and $R^{15}$ are identical or different and represent hydrogen, cyclopropyl, cyclopentyl, cyclohexyl, phenyl or (C$_1$–C$_5$)-alkyl, which is optionally substituted by cyclopropyl, cyclopentyl, cyclohexyl or phenyl, which for its part may be mono- to polysubstituted by identical or different substituents from the group consisting of fluorine, chlorine, bromine, hydroxyl or (C$_1$–C$_4$)-alkoxy,
$R^{16}$ represents hydrogen or (C$_1$–C$_3$)-alkyl,
$R^{17}$ represents hydrogen, adamantyl, cyclopropyl, cyclopentyl or cyclohexyl, or represents (C$_2$–C$_4$)-alkenyl or (C$_1$–C$_{10}$)-alkyl, which is optionally substituted by adamantyl, cyclopropyl, cyclopentyl, cyclohexyl, phenyl, phenoxy naphthyl, pyridyl, thienyl or furyl, where the ring systems for their part may be mono- to polysubstituted by identical or different substituents from the group consisting of (C$_1$–C$_4$)-alkyl, (C$_1$–C$_4$)-alkoxy, hydroxyl, nitro, fluorine, chlorine and bromine,
and/or alkyl is optionally substituted by a radical of the formula

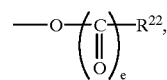

in which e represents a number 0 or 1 and
$R^{22}$ represents (C$_1$–C$_4$)-alkyl, phenyl or naphthyl, which are optionally mono- to polysubstituted by identical or different substituents from the group consisting of fluorine, chlorine, bromine, nitro, hydroxyl and (C$_1$–C$_4$)-alkoxy, or
represents phenyl, naphthyl, thienyl, furyl or pyridyl, which for their part may optionally be mono- to polysubstituted by identical or different substituents from the group consisting of (C$_1$–C$_4$)-alkoxy, (C$_1$–C$_4$)-alkyl, hydroxyl, nitro, fluorine, chlorine and bromine, or
represents a radical of the formula

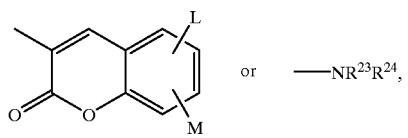

in which
L and M are identical or different and represent hydrogen fluorine, chlorine or bromine,
$R^{23}$ and $R^{24}$ have the meaning of $R^{10}$ and $R^{11}$ given above and are identical to or different from this meaning,
$R^{18}$ has the meaning of $R^{16}$ given above and is identical to or different from this meaning,
$R^{19}$ represents cyclopropyl, cyclopentyl or cyclohexyl, or represents (C$_1$–C$_7$)-alkyl or (C$_2$–C$_6$)-alkenyl, which for their part are optionally substituted by substituents selected from the group consisting of fluorine, chlorine, bromine, phenyl, hydroxyl, morpholinyl, cyclopropyl, cyclopentyl, cyclohexyl and by a group of the formula —SiR$^{25}$R$^{26}$R$^{27}$,
in which
$R^{25}$, $R^{26}$ and $R^{27}$ are identical or different and represent (C$_1$–C$_4$)-alkyl,
$R^{20}$ and $R^{21}$ are identical or different and represent hydrogen, adamantyl, cyclopropyl, cyclopentyl, cyclohexyl, phenyl, phenoxy-substituted phenyl, pyridyl, furyl, thienyl, thiazolyl or pyrryl, or
represent (C$_2$–C$_6$)-alkenyl, (C$_1$–C$_{10}$)-alkyl or (C$_3$–C$_6$)-alkinyl, which are optionally substituted by hydroxyl, cyclopropyl, cyclopentyl, cyclohexyl, (C$_1$–C$_5$)-alkoxy, (C$_1$–C$_6$)-alkoxycarbonyl, fluorine, chlorine, bromine, hydroxyl, trifluoromethyl, phenyl, pyridyl, furyl, thienyl or pyrryl, where the ring systems are optionally substituted up to 2 times by identical or different substituents from the group consisting of (C$_1$–C$_4$)-alkoxy, fluorine, chlorine, bromine, phenoxy, hydroxyl or (C$_1$–C$_4$)-alkyl,
and/or the alkyl listed under $R^{20}/R^{21}$ is optionally substituted by radicals of the formulae

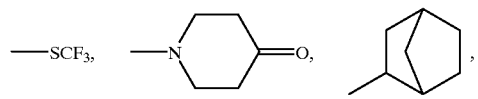

-continued

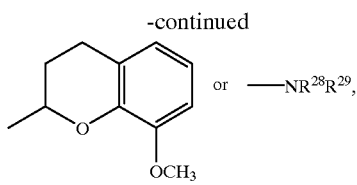

in which
R$^{28}$ and R$^{29}$ are identical or different and represent hydrogen or (C$_1$–C$_4$)-alkyl, or
represent a radical of the formula

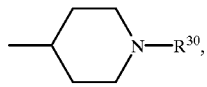

in which
R$^{30}$ has the meaning of R$^{12}$ given above and is identical to or different from this meaning, or
R$^{20}$ and R$^{21}$ together with the nitrogen atom form a radical of the formula

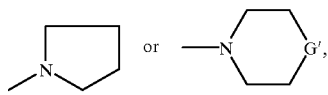

in which
G' has the meaning of G given above and is identical to or different from this meaning,
R$^2$ and R$^3$ are identical or different and represent hydrogen or (C$_1$–C$_3$)-alkyl, and
D and E together represent radicals of the formulae

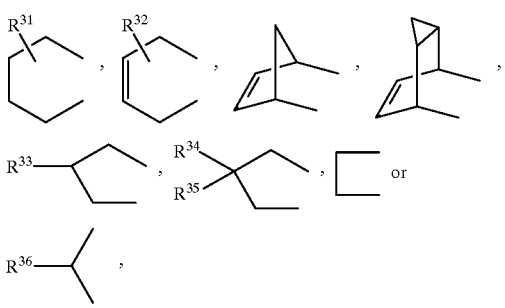

in which
R$^{31}$ and R$^{32}$ are identical or different represent hydrogen or (C$_1$–C$_4$)-alkyl,
R$^{33}$ represents hydrogen, hydroxyl, (C$_1$–C$_4$)-alkoxy, (C$_1$–C$_4$)-alkoxy-carbonyl, carboxyl or (C$_1$–C$_4$)-alkyl which is optionally substituted by hydroxyl carboxyl or (C$_1$–C$_4$)-alkoxycarbonyl, or represents a radical of the formula —OR$^{37}$,
in which
R$^{37}$ represents (C$_1$–C$_4$)-alkenyl or (C$_1$–C$_4$)-alkyl, which is optionally substituted by cyclopropyl, cyclopentyl, cyclohexyl or phenyl, which for its part may be substituted by trifluoromethyl, fluorine, chlorine, bromine or (C$_1$–C$_4$)-alkyl, or represents a radical of the formula —SO$_2$R$^{38}$,
in which
R$^{38}$ represents phenyl or methyl,
R$^{34}$ and R$^{35}$ are identical or different and represent fluorine, chlorine, hydroxyl, carboxyl, (C$_1$–C$_4$)-acyloxy or amino, or represent (C$_1$–C$_4$)-alkyl, which is optionally substituted by hydroxyl or (C$_1$–C$_4$)-acyloxy, or
R$^{34}$ and R$^{35}$ together with the adjacent ring carbon atom form a radical of the formula

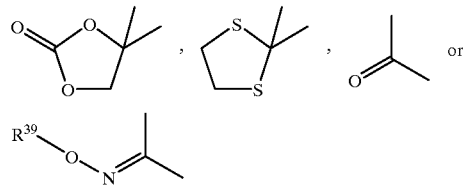

in which
R$^{39}$ represents hydrogen or methyl, and
R$^{36}$ represents (C$_1$–C$_4$)-alkoxycarbonyl or (C$_1$–C$_4$)-alkyl, which is optionally substituted up to 2 times by identical or different substituents from the group consisting of hydroxyl, (C$_1$–C$_5$)-alkoxy and (C$_1$–C$_4$)-alkoxycarbonyl,
and their pharmaceutically acceptable salts.

Particular preference is given to compounds of the general formula (I) according to the invention
in which
A represents radicals of the formulae —CH$_2$—, —CO—, —CR$^4$(OH)— or —(CH$_2$)$_a$—CHR$^5$—
in which
a represents a number 0, 1, 2 or 3,
R$^4$ represents hydrogen or (C$_1$–C$_3$)-alkyl and
R$^5$ represents phenyl, or
represents (C$_2$–C$_4$)-alkanediyl, propenediyl or (C$_2$–C$_3$)-alkinediyl,
R$^1$ represents hydrogen, cyclopropyl or cyclohexyl, or
represents benzofuranyl, benzothiophenyl, benzimidazolyl, thienyl, quinazolyl or quinoxalinyl, or
represents radicals of the formulae

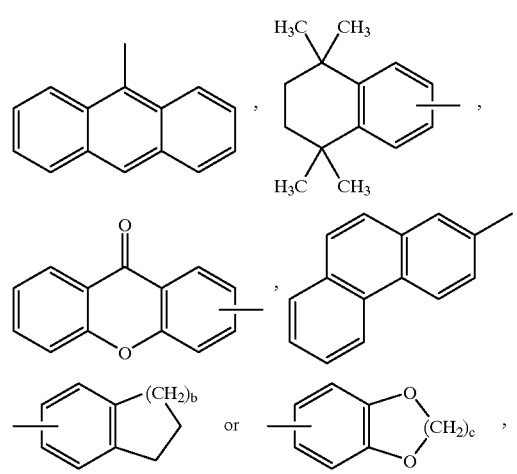

in which
b and c are identical or different and represent a number 1 or 2, or
represent phenyl or naphthyl,
where all of the ring systems listed above are optionally mono- to polysubstituted by identical or different substituents selected from the group consisting of fluorine, chlorine, bromine, iodine, cyano, nitro, trifluoromethyl or $(C_1–C_4)$-alkoxy, cyclohexyl, phenyl, phenoxy, pyridyl, pyrimidyl, pyridazinyl or benzyloxy, which for their part may be substituted up to three times by identical or different substituents from the group consisting of cyano, fluorine, chlorine, bromine and iodine.

and/or are substituted by $(C_1–C_4)$-alkyl and $(C_2–C_3)$-alkenyl, which for their part may be substituted by chlorine, bromine, iodine or phenyl or by radicals of the formula —$OR^9$ or —$NR^{10}R^{11}$ or

in which $R^9$ represents hydrogen or $(C_1–C_3)$-alkyl, and $R^{10}$ and $R^{11}$ are identical or different and represent hydrogen, phenyl or $(C_1–C_3)$-alkyl, which is optionally substituted by phenyl, which for its part may be substituted by chlorine, bromine, hydroxyl or $(C_1–C_3)$-alkoxy, or $R^{10}$ and $R^{11}$ together with the nitrogen atom form a radical of the formula

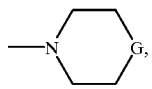

in which

G represents an oxygen atom or a radical of the formula —$NR^{12}$, in which $R^{12}$ represents hydrogen, phenyl, benzyl, $(C_1–C_3)$-alkyl, $(C_1–C_3)$-alkoxycarbonyl, pyridyl, pyrimidyl, pyridazinyl or furyl, and/or are substituted by groups of the formulae —$CO_2$—$R^{13}$, —$NR^{14}R^{15}$, —$NR^{16}CO$—$R^{17}$, —$NR^{18}CO_2$—$R^{19}$ and —CO—$NR^{20}R^{21}$, in which $R^{13}$ represents hydrogen, or represents $(C_1–C_6)$-alkyl or allyl, which for their part may be substituted by radicals of the formulae

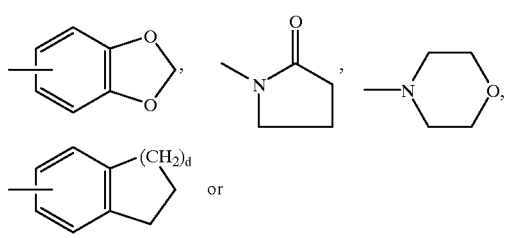

phenyl, naphthyl or pyridyl, in which d represents a number 1 or 2, or represents phenyl, which is optionally substituted by phenyl, which for its part may be substituted by cyano, chlorine or bromine, $R^{14}$ and $R^{15}$ are identical or different and represent hydrogen, cyclohexyl, phenyl or $(C_1–C_4)$-alkyl, which is optionally substituted by cyclopropyl, cyclohexyl or phenyl, which for its part may be mono- to polysubstituted by identical or different substituents from the group consisting of chlorine and $(C_1–C_3)$-alkoxy, $R^{16}$ represents hydrogen, methyl or ethyl, $R^{17}$ represents hydrogen, adamantyl, cyclopentyl or cyclohexyl, or represents $(C_2–C_3)$-alkenyl or $(C_1–C_8)$-alkyl, which is optionally substituted by adamantyl, cyclopropyl, cyclopentyl, cyclohexyl, phenyl, phenoxy, thienyl or furyl, where the ring systems for their part may be mono- to polysubstituted by identical or different substituents from the group consisting of $(C_1–C_3)$-alkyl, $(C_1–C_3)$-alkoxy, hydroxyl, nitro, fluorine, chlorine and bromine, and/or alkyl is optionally substituted by a radical of the formula

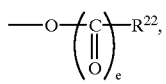

in which e is a number 0 or 1 and $R^{22}$ represents $(C_1–C_3)$-alkyl, phenyl or naphthyl, which are optionally mono- to polysubstituted by identical or different substituents from the group consisting of fluorine, chlorine, bromine, nitro, hydroxyl and $(C_1–C_3)$-alkoxy, or represents phenyl, naphthyl, thienyl or furyl, which for their part may optionally be mono- to polysubstituted by identical or different substituents from the group consisting of $(C_1–C_3)$-alkoxy, $(C_1–C_3)$-alkyl, nitro, fluorine, chlorine and bromine, or represents a radical of the formula

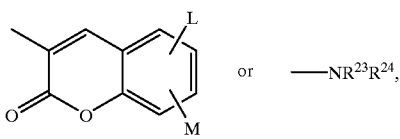

in which

L and M are identical or different and represent hydrogen, fluorine or chlorine, $R^{23}$ and $R^{24}$ have the meaning of $R^{10}$ and $R^{11}$ given above and are identical to or different from this meaning, $R^{18}$ has the meaning of $R^{16}$ given above and is identical to or different from this meaning, $R^{19}$ represents $(C_1–C_4)$-alkyl or $(C_3–C_5)$-alkenyl, which for their part are optionally substituted by substituents selected from the group consisting of chlorine, phenyl, hydroxyl, morpholinyl, cyclopropyl, cyclohexyl and by a group of the formula —$SiR^{25}R^{26}R^{27}$, in which $R^{25}$, $R^{26}$ and $R^{27}$ are identical and represent methyl, $R^{20}$ and $R^{21}$ are identical or different and represent hydrogen, adamantyl, cyclopropyl, cyclopentyl, cyclohexyl, phenyl, phenoxy-substituted phenyl, thiazolyl or pyrryl, or represent $(C_2–C_3)$-alkenyl, $(C_1–C_7)$-alkyl or $(C_3–C_5)$-alkinyl, which are optionally substituted by hydroxyl, cyclopropyl, cyclopentyl, cyclohexyl, $(C_1–C_3)$-alkoxy, hydroxyl, trifluoromethyl, phenyl, pyridyl, furyl, thienyl or pyrryl, where the ring systems are optionally substituted up to 2 times by identical or different substituents from the group consisting of $(C_1-C_3)$-alkoxy, $(C_1-C_6)$-alkoxycarbonyl, fluorine, chlorine, bromine, phenoxy, hydroxyl and $(C_1-C_3)$-alkyl, and/or the alkyl listed under $R^{20}/R^{21}$ is optionally substituted by radicals of the formulae

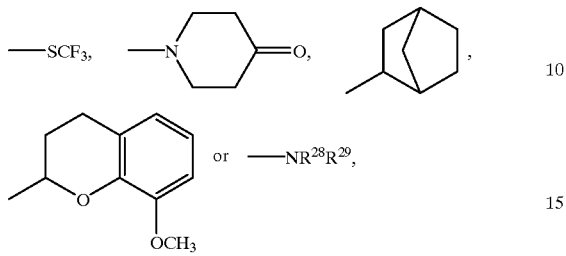

in which
$R^{28}$ and $R^{29}$ are identical or different and represent hydrogen or $(C_1-C_3)$-alkyl, or
$R^{20}$ or $R^{21}$ represent a radical of the formula

in which
$R^{30}$ has the meaning of $R^{12}$ given above and is identical to or different from this meaning,
$R^{20}$ and $R^{21}$ together with the nitrogen atom form a radical of the formula

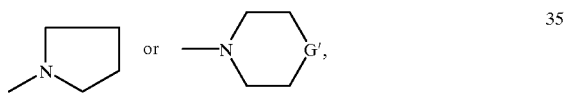

in which
G' has the meaning of G given above and is identical to or different from this meaning,
$R^2$ and $R^3$ are identical or different and represent hydrogen or methyl, and
D and E together represent radicals of the formulae

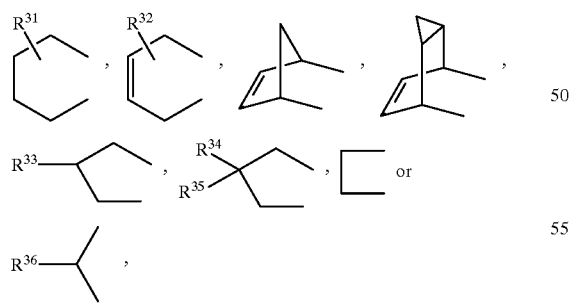

in which
$R^{31}$ and $R^{32}$ are identical or different represent hydrogen or $(C_1-C_3)$-alkyl,
$R^{33}$ represents hydrogen, hydroxyl, $(C_1-C_3)$-alkoxy, $(C_1-C_3)$-alkoxycarbonyl, carboxyl or $(C_1-C_3)$-alkyl, which is optionally substituted by hydroxyl or $(C_1-C_3)$-alkoxycarboxyl, or represents a radical of the formula $-OR^{37}$, in which
$R^{37}$ represents $(C_1-C_3)$-alkenyl or $(C_1-C_3)$-alkyl, which is optionally substituted by cyclopropyl, cyclopentyl, cyclohexyl or phenyl, which for its part may be substituted by trifluoromethyl, fluorine, chlorine, bromine or $(C_1-C_3)$-alkyl, or represents a radical of the formula $-SO_2R^{38}$,
in which
$R^{38}$ represents methyl,
$R^{34}$ and $R^{35}$ are identical or different and represent fluorine, chlorine, hydroxyl, carboxyl, $(C_1-C_3)$-acyloxy or amino, or represent $(C_1-C_3)$-alkyl, which is optionally substituted by hydroxyl or $(C_1-C_3)$-acyloxy, or
$R^{34}$ and $R^{35}$ together with the adjacent ring carbon atom form a radical of the formula

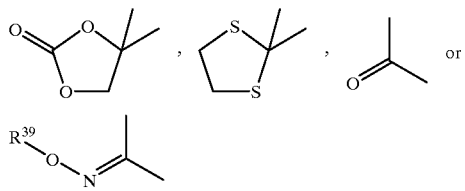

in which
$R^{39}$ represents hydrogen or methyl, and
$R^{36}$ represents $(C_1-C_3)$-alkoxycarbonyl or $(C_1-C_3)$-alkyl, which is optionally substituted up to 2 times by identical or different substituents from the group consisting of hydroxyl, $(C_1-C_4)$-alkoxy or $(C_1-C_3)$-alkoxycarbonyl, and their pharmaceutically acceptable salts.

Preference is likewise given to compounds of the general formula (I) according to the invention in which A represents the $-CH_2-$ group and $R^1$ represents phenyl, biphenyl or naphthyl.

Very particular preference is given to the structures listed in the table below:

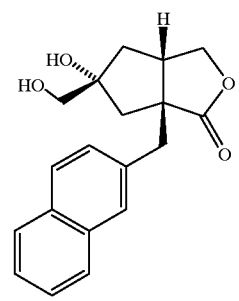

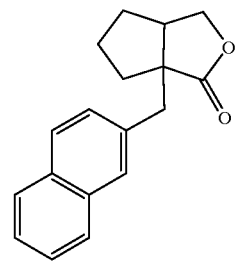

-continued

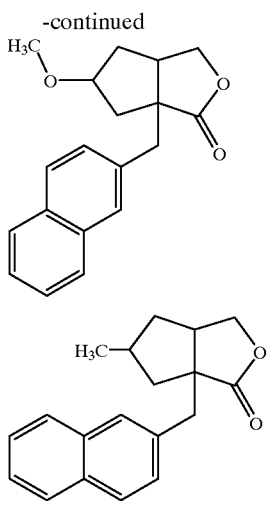

Moreover, processes for preparing the compounds of the general formula (I) according to the invention have been found which are characterized in that

[A] compounds of the general formula (II)

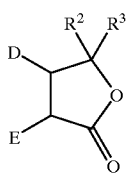

(II)

in which
D, E, $R^2$ and $R^3$ are as defined above,
are reacted with compounds of the general formula (III),

T—A—$R^1$     (III)

in which
T represents halogen, preferably bromine, and
A and $R^1$ are as defined above,
in inert solvents and in the presence of a base, or

[B] in the case that D and E together represent the radical
Ⴚ, compounds of the general formula (IV)

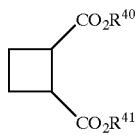

(IV)

in which
$R^{40}$ and $R^{41}$ are identical or different and represent $C_1$–$C_4$-alkyl,
are initially, as described under [A], reacted in the presence of a base with compounds of the general formula (III) to give compounds of the general formula (V)

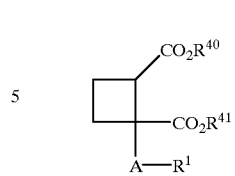

(V)

in which
$R^{40}$, $R^{41}$, A and $R^1$ are as defined above,
and then cyclized,
subsequently hydrolysed to give a monocarboxylic acid monoester [formula (V), $R^{40}$=H] and finally reduced in the presence of a reducing agent and cyclized to give a bicyclic lactone of the general formula (VI)

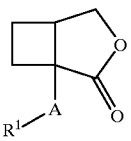

(VI)

in which
$R^1$ is as defined above,
and the substituent $R^1$ is, if appropriate, derivatized.
The process according to the invention can be illustrated in an exemplary manner by the formula scheme below:

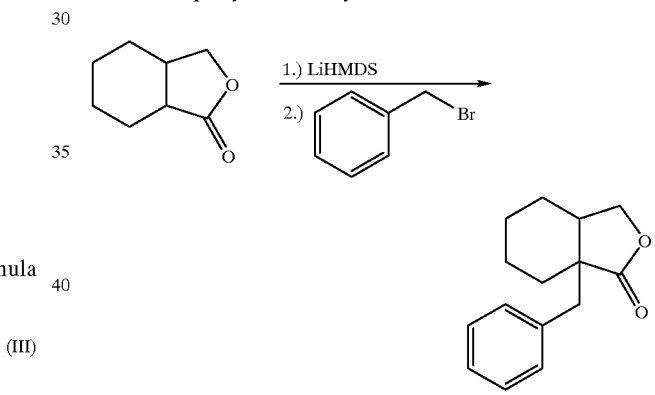

Suitable solvents are all inert solvents which do not change under the reaction conditions. These preferably include ethers, such as diethyl ether, dioxane, tetrahydrofuran, glycol dimethyl ether or diethylene glycol dimethyl ether. Particular preference is given to tetrahydrofuran.

Suitable bases are the customary inorganic or organic bases. These preferably include alkali metal hydroxides, such as, for example, sodium hydroxide or potassium hydroxide, or alkali metal carbonates such as sodium carbonate or potassium carbonate, or sodium methoxide or potassium methoxide, or sodium ethoxide or potassium ethoxide or potassium tert-butoxide, or amides, such as sodium amide, lithium bis-(trimethylsilyl)amide, lithium diisopropylamide, or organometallic compounds, such as butyllithium or phenyllithium. Preference is given to lithium diisopropylamide and lithium bis-(trimethylsilyl)amide.

Here, the base is employed in an amount of from 1 to 5, preferably from 1 to 2 mol, based on 1 mol of the compounds of the general formulae (II) and (V.

The reactions are generally carried out in a temperature range of from −78° C. to reflux temperature, preferably from −78° C. to −20° C.

The reactions can be carried out at atmospheric pressure or elevated or reduced pressure (for example from 0.5 to 5 bar). In general, the reactions are carried out at atmospheric pressure.

In the context of the invention, derivatizations which may be mentioned as being preferred are dihydroxylations, reductions and ether synthesis at the radical D and E. Starting with the exomethylene-substituted bicycles, the corresponding dihydroxy compounds are prepared with osmium tetroxide/N-methylmorpholine N-oxide in inert solvents, and the corresponding reduced compounds are prepared with hydrogen in the presence of a catalyst in inert solvents. Likewise, it is possible, starting from hydroxy-substituted bicycles, to introduce the ether functions using the corresponding alkyl halides in the presence of bases.

The derivatizations can be illustrated in an exemplary manner by the following formula scheme:

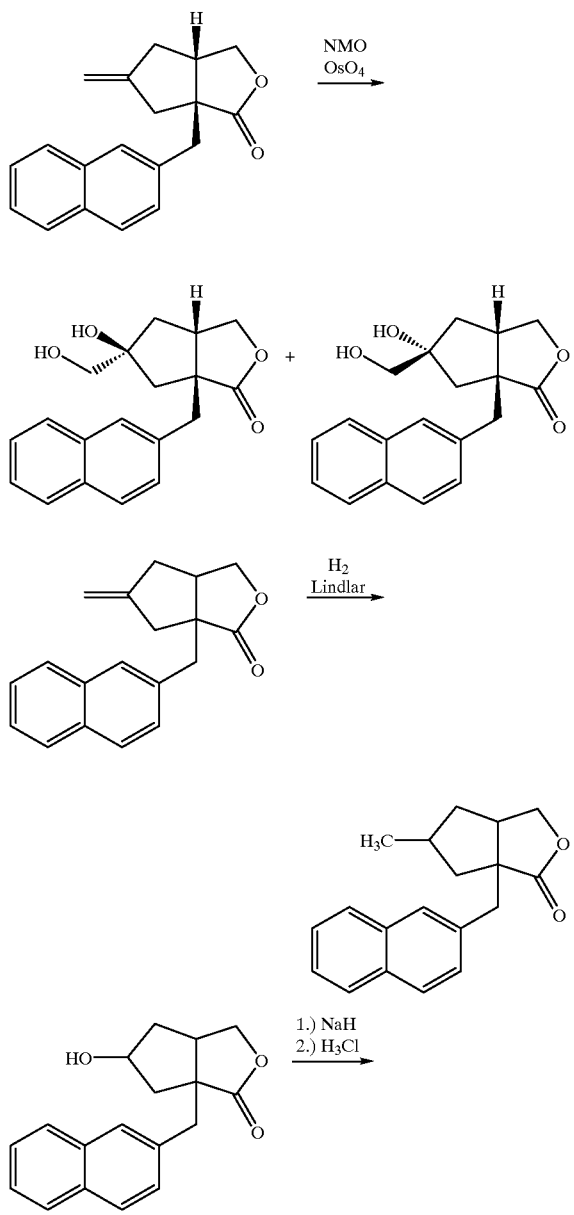

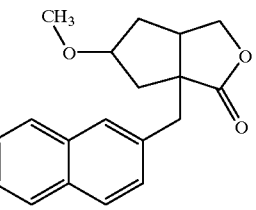

Here, suitable solvents are inert organic solvents which do not change under the reaction conditions. These include halogenated hydrocarbons, such as dichloromethane, trichloromethane, carbon tetrachloride, 1,2-dichloromethane, trichloroethane, tetrachloroethane, 1,2-dichloroethane or trichloroethylene, hydrocarbon, such as benzene, xylene, toluo, hexane, cyclohexane, or mineral oil fractions, nitromethane, dimethylformamide, acetonitrile or hexamethylphosphoric triamide. It is also possible to use mixtures of the solvents. Particular preference is given to dichloromethane.

Suitable bases for the derivatizations are the customary basic compounds. These preferably include alkali metal or alkaline earth metal hydroxides, such as lithium hydroxide, sodium hydroxide, potassium hydroxide or barium hydroxide, alkali metal hydride, such as sodium hydride, alkali metal or alkaline earth metal carbonates, such as sodium carbonate, potassium carbonate, or alkali metal alkoxides, such as, for example, sodium methoxide, sodium ethoxide, potassium methoxide or potassium ethoxide, or potassium tert-butoxide, or organic amines, such as benzyl-trimethylammonium hydroxide, tetrabutylammonium hydroxide, pyridine, triethylamine or N-methylpiperidine.

The derivatizations are generally carried out in a temperature range from −20° C. to 150° C., preferably at from 0° C. to 25° C.

The derivatizations are generally carried out under atmospheric pressure. However, it is also possible to carry out the processes under reduced pressure or under elevated pressure (for example in a range from 0.5 to 5 bar).

When carrying out the derivatizations, the bases are generally employed in an amount of from 1 to 3 mol, preferably from 1 to 1.5 mol, based on 1 mol of the carboxylic acid in question.

The compounds of the general formulae (II) and (III) are known per se or can be prepared by customary methods.

The compounds of the general formula (I) according to the invention are suitable for use as medicaments in the treatment of humans and animals.

The compounds of the general formula (I) according to the invention are suitable for modulating metabotropic glutamate receptors and therefore influence the glutamatergic neurotransmitter system.

For the purpose of the invention, a modulator of the metabotropic glutamate receptor is an agonist or antagonist of this receptor.

The compounds according to the invention are particularly suitable as modulators of the metabotropic glutamate receptor of subtype 1, very particularly as antagonists of this receptor subtype.

Owing to their pharmacological properties, the compounds according to the invention can be used, on their own or in combination with other pharmaceuticals, for the treatment and/or prevention of neuronal damage or disorders associated with a decompensation of the physiological or with pathophysiological conditions of the glutamatergic system in the central and peripheral nervous system.

For the treatment and/or prevention of neuronal damage caused, for example, by ischaemic, thromb- and/or thrombemolic, and haemorrhagic stroke, conditions after direct and indirect injuries in the area of the brain and the skull. Furthermore for the treatment and/or prevention of cerebral ischaemias after all surgical interventions in the brain or peripheral organs or body parts and conditions of pathogenic or allergic nature accompanying or preceding them, which can lead primarily and/or secondarily to neuronal damage.

Likewise, the compounds according to the invention are also suitable for the therapy of primary and/or secondary pathological conditions of the brain, for example during or after cerebral vasospasms, hypoxia and/or anoxia of previously unmentioned origin, perinatal asphyxia, autoimmune disorders, metabolic and organ disorders which can be accompanied by damage to the brain, and also damage to the brain as a result of primary brain disorders, for example convulsive conditions and artero- and/or arteriosclerotic changes. For the treatment of chronic or psychiatric conditions such as, for example, depression, neurodegenerative disorders, such as, for example, Alzheimer's, Parkinson's or Huntington's disease, multiple sclerosis, amyotrophic lateral sclerosis, neurodegeneration due to acute and/or chronic viral or bacterial infections and multiinfarct dementia.

Moreover, they can be used as pharmaceuticals for the treatment of dementias of different origin, impaired brain performance owing to old age, memory disturbances, spinal injuries, states of pain, states of anxiety of different origin, medicament-related Parkinson's syndrome, psychoses (such as, for example, schizophrenia), brain oedma, neuronal damage after hypoglycaemia, emesis, nausea, obesity, addiction and withdrawal syndromes, CNS-mediated spasms, sedation and motor disturbances.

Furthermore, the compounds of the general formula (I) according to the invention can be used for promoting neuronal regeneration in the post-acute phase of cerebral injuries or chronic disorders of the nervous system.

They are preferably employed as pharmaceuticals for the treatment of cerebral ischaemias, cranial cerebral trauma, states of pain or CNS-mediated spasms (such as, for example, epilepsy).

The modulation of substances at the metabotropic glutamate receptor (direct or indirect effect on the coupling efficiency of the glutamate receptor to G-proteins) can be examined using primary cultures of granular cells from the cerebellum. Electrophysiological measurements on these cell cultures in the "cell attached" mode show that L-type $Ca^{2+}$-channels in this preparation are activated by mGluR1-glutamate receptors (J. Neurosci. 1995, 15, 135), whereas they are blocked by group II receptors (J. Neurosci. 1994. 14, 7067–7076). By an appropriate experimental arrangement, it is possible to monitor the modulatory effect of pharmacological test substances on glutamate receptors. Detailed examination of subtype specificity under controlled conditions can be carried out by injecting the appropriate mGluR subtype DNA into Xenopus oocytes (WO 92/10583).

Using the test models below, it is possible to demonstrate the antiischaemic activity of the compounds in vivo.
Permanent Focal Cerebral Ischaemia in the Rat (MCA-O)

Under isoflurane anaesthesia, the medium cerebral artery is exposed on one side and the latter and its side branches are irreversibly sealed by means of electrocoagulation. As a result of the intervention a cerebral infarct is formed. During the operation, the body temperature of the animal is kept at 37° C. After wound closure and wearing off of the anaesthesia, the animals are again released into their cage. The administration of substance is carried out according to different time schemes and via different administration routes (i.v., i.p.) after occlusion. The infarct size is determined after 7 days. To do this, the brain is removed, worked up histologically and the infarct volume is determined with the aid of a computer-assisted analysis system.
Subdural Haematoma in the Rat (SDH)

Under anaesthesia, the animal's own blood is injected subdurally on one side. An infarct is formed under the haematoma. Substance administration is carried out according to different time schemes and via different administration routes (i.v., i.p.). The determination of the infarct size is carried out as described in the model of permanent focal ischaemia in the rat (MCA-O).

Using the method described in NeuroReport 1996, 7, 1469–1474, it is possible to test for antiepileptic activity.

The suitability of the compounds according to the invention for testing can be determined by the methods described in Science 1998, 281, 1349–1352 and Eur. J. Pharmacol. 1996, 316, 129–136.

The present invention includes pharmaceutical preparations which, in addition to inert, non-toxic, pharmaceutically suitable auxiliaries and excipients, comprise one or more compounds of the general formula (I), or which consist of one or more active compounds of the formula (I), and processes for producing these preparations.

In these preparations, the active compounds of the formula (I) should be present in a concentration of from 0.1 to 99.5% by weight, preferably from 0.5 to 95% by weight, of the total mixture.

In addition to the active compounds of the formula (I), the pharmaceutical preparations may also comprise other pharmaceutically active compounds.

The abovementioned pharmaceutical preparations can be prepared in a customary manner by known methods, for example with the auxiliary/auxiliaries or excipient(s).

In general, it has proved advantageous to administer the active compound(s) of the formula (I) in total amounts of about 0.01 to about 100 mg/kg, preferably in total amounts of about 1 mg/kg to 50 mg/kg, of body weight per 24 hours, if appropriate in the form of a plurality of individual administrations, to achieve the desired result.

However, if appropriate, it may be advantageous to depart from the amounts mentioned, namely depending on the type and on the body weight of the object treated, on the individual response towards the medicament, the nature and severity of the disorder, the manner of formulation and administration, and the time or interval at which administration takes place.

General Section

Mobile Phases for Chromatography
I Dichloromethane/methanol
II Dichloromethane/ethanol
III Cyclohexane/ethyl acetate
IV Cyclohexane/dichloromethane
V Butyl acetate (200), butanol (26), acetic acid (100), phosphate buffer pH=6 (60)
Abbreviations
DME 1,2-Dimethoxyethane
HMPA Hexamethylphosphoric triamide
LiHMDS Lithium bistrimethylsilylamide
LDA Lithium diisopropylamide
MTBE Methyl tert-butyl ether
THF Tetrahydrofuran

STARTING MATERIALS

Example 1A cis-8-Oxabicyclo[4.3.0]nonan-9-one

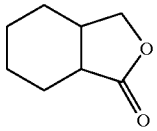

With stirring and ice-cooling, 80 ml of a solution of cis-cyclohexane-1,2-dicarboxylic anhydride (15.4 g, 100 mmol) in THF are added over a period of 10 min to a mixture of sodium borohydride (3.8 g, 100 mmol) in 20 ml of THF. The ice-bath is removed and the mixture is stirred for 2 h. 40 ml of 6 N hydrochloric acid are added carefully and the mixture is concentrated. 200 ml of water are added and the aqueous phase is extracted with ether. The organic phase is dried, filtered, concentrated and distilled under reduced pressure (123° C., 13 mm; 75° C., 0.5 mm).

Yield: 13.7 g (97%).

MS (CI): m/e=141 [M+H$^+$]

Example 2A cis-8-Oxabicyclo[4.3.0]non-3-en-9-one

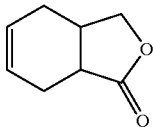

Cis-Cyclohexene-1,2-dicarboxylic anhydride (30.4 g, 200 mmol) in methanol (9 ml, 220 mmol) is heated at the boil for 1 h. Excess solvent is then evaporated. 33.2 g (180 mmol) of the resulting monomethyl ester are, at 0° C. and under argon, dissolved in 200 ml of dry dichloromethane and admixed dropwise with oxalyl chloride (32 g, 252 mmol). After the evolution of gas has ceased, stirring at room temperature is continued for 3 h. The solvent is then removed under reduced pressure and the residue is dissolved in 75 ml of THF. This solution is then added dropwise to a solution, kept at −40° C. and under argon, of sodium borohydride (13.6 g, 360 mmol) in 750 ml of absolute ethanol. After the evolution of gas has ceased, stirring at −40° C. is continued for 2 h, and the mixture is acidified to pH 2 using 4 N sulphuric acid and concentrated. The residue is admixed with 400 ml of water and extracted with MTBE. The ether phases are dried over magnesium sulphate, filtered and concentrated. The residue is then taken up in 200 ml of toluene, admixed with 10-camphorsulphonic acid (100 mg, 0.43 mmol) and heated in a water separator until TLC shows complete conversion. The solvent is then evaporated and the residue is distilled under reduced pressure (b.p.: 70° C./0.01 Torr).

Yield: 21.5 g (86.4%)

R$_f$ (VII)=0.67

MS (CI): m/e=139 [M+H$^+$]

Example 3A cis-4-Methyl-8-oxabicyclo[4.3.0]nonan-9-one

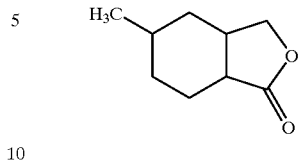

With stirring and ice-cooling, 80 ml of a solution of 4-methylcyclohexane-1,2-dicarboxylic anhydride (16.8 g, 100 mmol) in THF are added over a period of 10 min to a mixture of sodium borohydride (3.8 g, 100 mmol) in 20 ml of THF. The ice-bath is removed and the mixture is stirred for 2 h. 40 ml of 6 N HCl are then added carefully and the mixture is concentrated. The residue is mixed with 200 ml of water and the aqueous phase is extracted with MTBE. The combined organic phases are then washed twice more with saturated sodium bicarbonate solution, dried over magnesium sulphate, filtered and concentrated. Purification is carried out by distillation under reduced pressure. Yield: 10.3 g (65.3%).

MS (CI): m/e=155 [M+H$^+$]

Example 4A cis-4-Oxa-tricyclo[5.2.1.0$^{2.6}$]dec-8-en-3-one

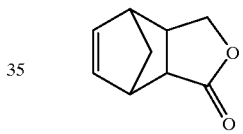

cis-Bicyclo[2.2.1]hept-5-ene-2,3-dicarboxylic anhydride (32.8 g, 200 mmol) in methanol (9 ml, 220 mmol) is heated at the boil for 1 h. Excess solvent is then evaporated. Under argon and at 0° C., 13.5 g (74.3 mmol) of the resulting monomethyl ester are dissolved in 90 ml of dry dichloromethane and admixed dropwise with oxalyl chloride (8.8 ml, 104 mmol). After the evolution of gas has ceased, stirring at room temperature is continued for 3 h. The solvent is then removed under reduced pressure and the residue is dissolved in 35 ml of THF. This solution is then added dropwise to a solution, kept at −40° C. and under argon, of sodium borohydride (5.5 g, 136 mmol) in 340 ml of absolute ethanol. After the evolution of gas has ceased, stirring at −40° C. is continued for 2 h, and the mixture is acidified to pH 2 using 4 N sulphuric acid and concentrated. The residue is admixed with 400 ml of water and extracted with MTBE. The ether phases are dried over magnesium sulphate, filtered and concentrated. The residue is then taken up in 65 ml of toluene, admixed with 35 mg of 10-camphorsulphonic acid and heated in a water separator until TLF shows complete conversion. The solvent is then evaporated and the residue is distilled under reduced pressure.

Yield: 6.4 g (57.4.%)

R$_f$ (VII)=0.33

MS (CI): m/e=151 [M+H$^+$]

Example 5A cis-4-Oxa-tricyclo[5.2.2.0$^{2,6}$]undec-8-en-3-one

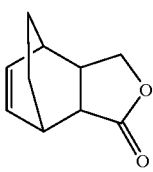

With stirring and ice-cooling, 23 ml of a solution of cis-bicyclo[2.2.2]oct-5-ene-2,3-dicarboxylic anhydride (5.5 g, 30.9 mmol) in THF are added over a period of 10 min to a mixture of sodium borohydride (1.1 g, 30.9 mmol) in 8 ml of THF. The ice-bath is removed and the mixture is stirred for 3 h. 12 ml of 6 N HCl are then added carefully and the mixture is concentrated. 100 ml of water are added and the aqueous phase is extracted with MTB ether. The organic phase is washed with saturated sodium bicarbonate solution, dried over magnesium sulphate and filtered and concentrated.

Yield: 4.8 g (94.7%)

$R_f$ (VII)=0.68

MS (CI): m/e=165 [M+H$^+$]

Example 6A cis-4-Oxa-tetracyclo-[5.3.2.0$^{2,6}$0$^{8,10}$]dodec-11-en-3-one

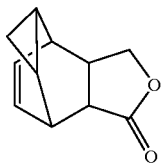

Tricyclo[3.2.2.0$^{2,4}$]non-8-ene-6,7-dicarboxylic anhydride (35.2 g, 200 mmol) in methanol (9 ml, 220 mmol) is heated at the boil for 1 h. The excess solvent is then evaporated. Under argon and at 0° C., 37.4 g (180 mmol) of the resulting monomethyl ester are dissolved in 200 ml of dry dichloromethane and admixed dropwise with oxalyl chloride (21 ml, 250 mmol). After the evolution of gas has ceased, stirring at room temperature is continued for 3 h. The solvent is then removed under reduced pressure and the residue is dissolved in 95 ml of THF. This solution is then added dropwise to a solution, kept at −40° C. and under argon, of sodium borohydride (13.6 g, 360 mmol) in 750 ml of absolute ethanol. After the evolution of gas has ceased, stirring is continued at −40° C. for 2 h, and the mixture is acidified to pH 2 using 4 N sulphuric acid and concentrated. The residue is admixed with 400 ml of water and extracted with MTBE. The ether phases are dried over magnesium sulphate, filtered and concentrated. The residue is then taken up in 200 ml of toluene, admixed with 10-camphorsulphonic acid (100 mg, 0.43 mmol) and heated in a water separator until TLC shows complete conversion. The solvent is then evaporated and the residue distilled under reduced pressure.

Yield: 11.4 g (36.0%)

$R_f$ (VII)=0.64

MS (CI): m/e=177 [M+H$^+$]

Example 7A 3-(2-Napththylmethyl)-5H-furan-2-one

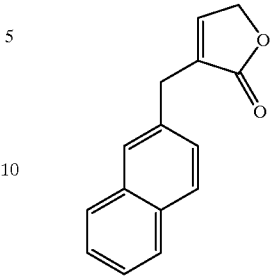

Butyllithium (60 ml, 150 mmol, 2.5 M in THF) is added to furyl tetramethylphosphorodiamidate (30 g) 137.5 mmol) in 170 ml of dry THF, under argon, cooled to −78° C., at such a rate that the internal temperature does not exceed −60° C. The resulting solution is once more cooled to −78° C. and, after 10 min, a solution of 2-bromomethylhaphthalene (38 g, 171.9 mmol) in 60 ml of THF is added dropwise over a period of 5 min, during which the temperature should not exceed −55° C. The mixture is then warmed to 0° C. and concentrated to about 50 ml. 75 ml of water and 125 ml of ethyl acetate are added, the phases are separated and the dark aqueous phase is extracted twice with in each case 50 ml of ethyl acetate. The combined organic phases are washed with sat. NaCl solution, dried over magnesium sulphate, filtered and concentrated. In an ice-bath, the residue is mixed with 60 ml of formic acid, and the mixture is stirred until the evolution of gas has ceased (about 45 min, ice-bath removed after 10 min); 125 ml of toluene are added and the solution is concentrated under reduced pressure. The residue is admixed with 250 ml of ethyl acetate and 75 ml of a salt solution (37 g of NaCl and 22 g of NaCO$_3$, dissolved in 200 ml of water). The organic phase is separated off and washed twice with in each case 45 ml of the salt solution, the wash phases are washed with ethyl acetate and the combined organic phase is dried over magnesium sulphate, filtered and concentrated. Purification by column chromatography (cyclohexane:ethyl acetate 20:1, then 3:1).

Yield 11.9 g (38.6%).

$R_f$ (VI)=0.17

MS (CI): m/e=225 [M+H$^+$]

Example 8A (3aS*,6aR*)-5-Methylidene-hexahydro-cyclopenta[c]furan-1-one

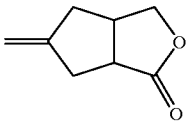

At −15° C., a solution of 2-methoxycarbonyl-4-methylidenecyclopentanecarboxylic acid (189.2 g; 1.027 mol) in THF (1 L) was admixed with triethylamine (156.6 ml; 1.130 mol) and ethyl chloroformate (18.2 ml; 1.027 mol), and the reaction mixture was stirred at room temperature for 1 h. The precipitate was filtered off with suction and the filtrate was concentrated, taken up in methanol (1 L), NaBH$_4$ (97.146 g; 2.568 mol) was added a little at a time at −15° C. and the mixture was stirred at room temperature for 1 h. For work-up, the mixture was admixed with 1 N HCl, saturated with NaCl and extracted with ethyl acetate. The combined organic phases were dried (Na₂SO₄) and concentrated, and the crude product was purified by chromatography.

Yield: 82.03 g (58%)

R_f (II, 50:1) 0.42

MS (EI): m/e=138 [M⁺]

Example 9A

3aS*,6aS*)-6a-Naphthalen-2-yl-5-methylidene-hexahydro-cyclopenta[c]furan-1-one

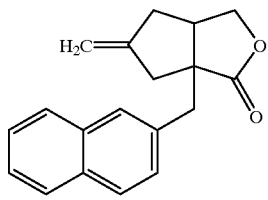

At −78° C., a solution of the compound from Example 8A (7.0 g, 50.66 mmol) in toluene (25 ml) was added to a solution of LiHMDS (1M in THF, 50.7 ml, 50.7 mmol) diluted with toluene (50 ml). The mixture was allowed to warm to room temperature, stirred for another 60 min and then admixed with the alkylating agent (2-naphthylmethyl bromide, 8.62 g, 38.97 mmol). After 14 h at room temperature, NH₄—Cl solution was added and the aqueous phase was extracted with ethyl acetate via a frit, purified by MPLC;

Yield: 7.33 mg (52%)

R_f (III, 5:1)=0.34

MS (EI): m/e=278 [M+H⁺]

The enantiomers (Example 10A fraction 1, and Example 10B fraction 2) were isolated by preparative HPLC (Chiralpak AS, isopropanol/petroleum ether 40–70° C. 20:80).

Example 10A di-n-Butyl cis-cyclobutane-1,2-dicarboxylate

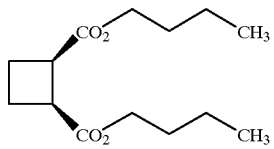

1 g (6.94 mmol) of cis-cyclobutane-1,2-dicarboxylic acid in 50 ml of n-butanol were heated under reflux with 0.3 g of conc. H₂SO₄ for 90 min. The mixture was then concentrated to about 5 ml and poured into dil. NaHCO₃ solution, extracted with ethyl acetate, dried over sodium sulphate and concentrated. Purification was carried out chromatographically over silica gel (mobile phase: petroleum ether:ethyl acetate 100:2>100:5).

¹H-NMR (200 Mhz; [d⁶]-DMSO) δ [ppm]: 0.9 (t; 6H), 1.48 (m; 4H), 1.60 (q; 4H), 2.20 (m; 2H), 2.38 (m; 2H), 4.07 (dt; 2H), 4.08 (dt; 2H).

Example 11A di-n-Butyl 1-(naphth-2-ylmethyl)-cis-cyclobutane-1,2-dicarboxylate

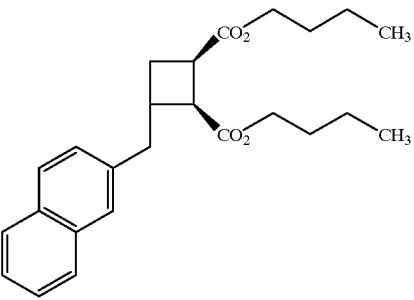

Under argon, 0.77 g (3 mmol) of di-n-butyl cis-cyclobutane-1,2-dicarboxylate was dissolved in 15 ml of dry THF, and the mixture was cooled to −70° C. 3.3 ml of a 1 molar solution of lithium bis-(hexamethyldisilazide) in THF are added dropwise at −70° C., and 0.73 g (3 mmol) of 2-(bromomethyl)-naphthalene is then added all at once. The mixture is allowed to warm rapidly to room temperature and stirred another 16 h. The mixture is then admixed with ammonium chloride solution, extracted three times with ethyl acetate, dried over sodium sulphate and concentrated. Purification is carried out chromatographically over silica gel (mobile phase: petroleum ether/ethyl acetate 100:3.5). Yield 0.49 g (41.2%).

¹H-NMR (200 Mhz; CDCl₃) δ [ppm]: 0.89 (t; 3H), 0.93 (t; 3H), 1.38 (br m; 4H), 1.55 (br m; 4H), 1.9–2.5 (br m; 4H), 3.2 (dd; 1H), 3.24 (d; 1H), 3.30 (d; 1H), 4.06 (t; 2H), 4.07 (t; 4H), 7.28 (dd; 1H), 7.47 (m; 2H), 7.63 (s; 1H), 7.73–7.82 (m: 3H).

MS (ESI)[m/e]: 397 (32; M+H), 323 (60, M—OC₄H₉), 249 (100, 323-C₄H₉OH).

Example 12A

Mono-n-butyl 1-(naphth-2-ylmethyl)-cis-cyclobutane-1,2-dicarboxylate

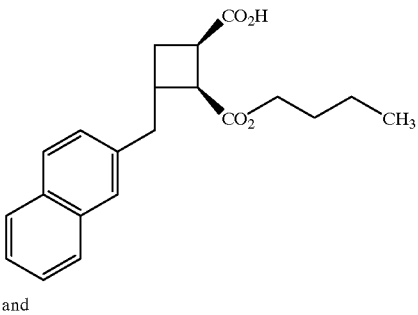

and

-continued

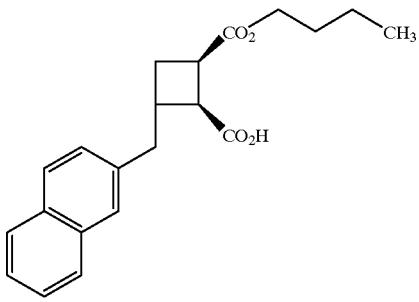

0.5 g (1.26 mmol) of di-n-butyl 1-(naphth-2-ylmethyl)-cis-cyclobutane-1,2-dicarboxylate was stirred in 15 ml of conc. hydrochloric acid for 3 h. The mixture was then concentrated and dried under high vacuum. The product was reacted further in crude form.

PREPARATION EXAMPLES

Example 1 and Example 2
(3aS*,5R*,6aS*)-5-Hydroxy-5-hydroxymethyl-6a-naphthalen-2-ylmethylhexahydro-cyclopenta[c]furan-1-one (Example 1) and (3aS*,5S*,6aS*)-5-hydroxy-5-hydroxymethyl-6a-naphthalen-2-ylmethylhexahydro-cyclopenta[c]furan-1-one (Example 2)

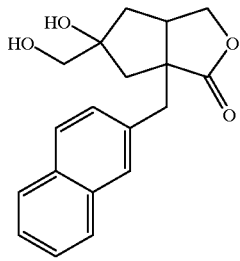

A mixture of the compound from Example 9A (1.0 g; 3.59 mmol), N-methyl-morpholine N-oxide (0.84 g: 7.2 mmol), osmium tetroxide (2.5% in t-butanol; 1.34 ml) in acetone/water (9:1, 27 ml) was stirred at 0° C. for 2 h. The mixture was admixed with 40% aqueous $NaHCO_3$ solution (0.6 ml), stirred for another 30 minutes, admixed with ethyl acetate and 1 N HCl, and the aqueous phase was saturated with sodium chloride and extracted with ethyl acetate. The combined organic phases ere dried ($MgSO_4$), the solvents were stripped off, the residue was mixed with dichloromethane and the precipitate was separated off.

Yield: 463 mg (41%, diastereomer A).

The filtrate is concentrated and the residue is purified by MPLC.

Yield: 335 mg (29%, diastereomer B) and 85 mg (19%, diastereomer A).

Example 1

(Diastereomer A)
$R_f$ (I, 20:1)=0.16
MS (DCI/$NH_3$): m/e=330 [M+$NH_4^+$]

Example 2

(Diastereomer B)
$R_f$ (I, 20:1)=0.16
MS (EI): m/e=335 [M+$Na^+$]

Example 3 and Example 4
(+)-(3aS,5R,6aS)-5-Hydroxy-5-hydroxymethyl-6a-naphthalen-2-ylmethylhexahydro-cyclopenta[c]furan-1-one (Example 3) and (−)-(3aS,5S,6aS)-5-hydroxy-5-hydroxymethyl-6a-naphthalen-2-ylmethylhexahydro-cylcopental[c]furan1-one (Example 4)

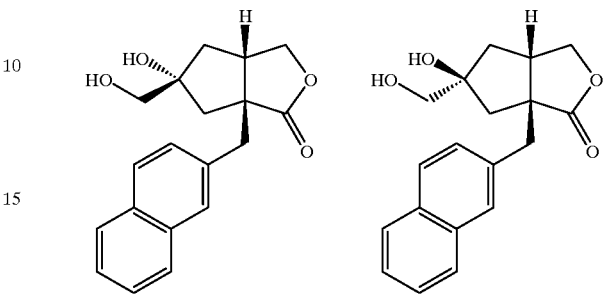

Analogously to the procedure of Examples 1 and 2, the title compound was prepared from the compound of Example 10A (418 mg, 1.5 mmol);

Example 3

Yield: 159 mg (34%, diastereomer A)
$[\alpha]_D^{20}$=+12.4 (c=0.54, $CH_2Cl_2$/MeOH 2:1)

Example 4

Yield: 216 mg (46%, diastereomer B)
$[\alpha]_D^{20}$ =−14.7 (c=0.73, $CH_2Cl_2$/MeOH 2:1)

Example 5
(3a"*,5"R*,6a"S*)-(5-Hydroxy-6a-naphthalen-2-ylmethyl-hexahodrocyclopenta[c]furan-1-on-5-yl)-methyl acetate

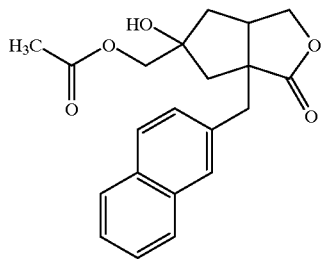

At 0° C., a solution of the compound from Example 1 (diastereomer A, 80 mg, 0.26 mmol) and triethylamine (90.7 mg, 0.90 mmol) in THF (10 ml) is admixed with acetyl chloride (60.3 mg, 0.77 mmol), and the reaction mixture is stirred at room temperature for 20 h. The mixture is poured into ethyl acetate and buffer solution (pH=2), the organic phase is washed with buffer solution (pH=2) and dried ($MgSO_4$), and the solvents are stripped off. The residue is purified by MPLC;

Yield: 93 mg (92%)
$R_f$ (II, 20:1)=0.46
MS: (ESI): m/e=377 [M+$Na^+$]

Example 6 and Example 7
(3a"S*,5"R*,6a"S*)-(5-Acetoxy-6a-naphthalen-2-ylmethylhexahydro-cyclopenta[c]furan-1-on-5-yl)-methyl acetate (Example 6) and (3a"S*,5"S*,6a"S)(5-acetoxy-6a- naphthalen-2-ylmethylhexahydro-cyclopenta[c]furan-1-on-5-yl)methyl acetate (Example 7)

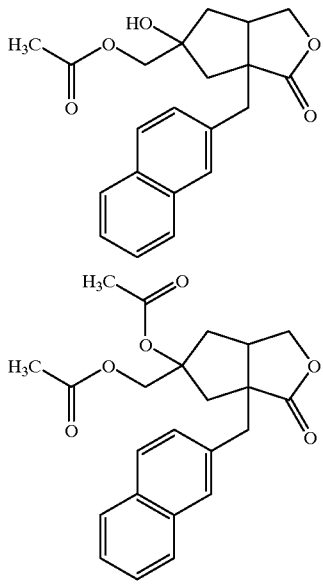

Analogously to Example 5, the title compounds were prepared from the compound of Example 2 (diastereomer B 80 mg, 0.256 mmol);

Example 6

Yield: 6 mg (6%, diacetate)

$R_f$ (II, 20:1)=0.51

MS (DCI/NH$_3$): m/e=456 [M+NH$_4^+$]

Example 7

Yield: 55 mg (66%, monoacetate)

$R_f$ (II) 20:1)=0.34

MS (DCI/NH$_3$): m/e=414 [M+NH$_4^+$]

Example 8

(3aS*,5R*,6aS*)-(6a-Naphthalen-2-ylmethyl-hexahydro-cyclopenta[c]furan-1-one)-5-spiro-4'-(1,3-dioxolan-2-one)

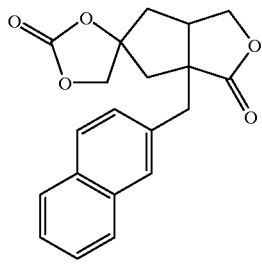

A solution of the compound from Example 1 (diastereomer A, 80 mg, 0.26 mmol) and carbonyldiumidazole (40 mg, 0.26 mmol) in THF (10 ml) was heated under reflux for 24 h. The resulting precipitate was filtered off with suction and dried;

Yield: 70 mg (80%)

$R_f$ (II, 20:1)=0.27

Example 9

(3aS*,5S*,6aS*)-(6a-Naphthalen-2-ylmethylmethyl-hexahydro-cyclopenta[c]furan-1-one)-5-spiro-4'-(1,3-dioxolan-2-one)

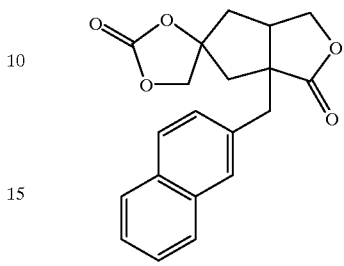

Analogously to Example 8, the title compound was prepared from the compound of Example 2 (diastereomer B, 80 mg, 0.256 mmol);

Yield: 30 mg (35%)

$R_f$ (II, 20:1)=0.60

Example 10

(3aS*,6aS*)-6a-Naphthalen-2-ylmethyl-hexahydro-cyclopenta[c]furan-1,5-dione

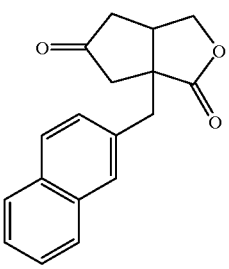

Analogously to Example 1 and 2, the compound from Example 9A (14.61 g, 52.49 mmol) was reacted with N-methylmorpholine N-oxide (12.29 g, 104.97 mmol) and osmium tetroxide (2.5% in t-butanol, 17.8 ml). The crude product was taken up in acetone (500 ml) and water (250 ml), admixed at 0° C. with sodium periodate (16.83 g, 78.73 mmol) and stirred at room temperature for 14 h. The resulting precipitate was filtered off with suction, the filtrate was concentrated and the residue was purified by MPLC;

Yield: 13.55 g (92%)

$R_f$ (II, 20:1)=0.57

MS (DCI/NH$_3$): m/e=298 [M+NH$_4^+$]

Example 11
(3aS*,6aS*)-(6a-Naphthalen-2-ylmethylmethyl-hexahydro-cyclopenta[c]furan-1-one)-5-spiro-2'-(1,3-dithiane)

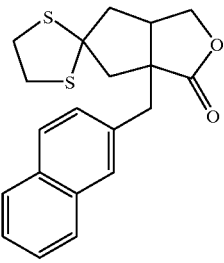

A solution of the compound from Example 10 (280 mg, 1.0 mmol) and ethanedithiol (0.941 g, 10.0 mmol) in toluene (20 mL) was admixed with boron trifluoride-diethyl ether complex (27 μl) and stirred at room temperature for 4 days. The mixture was poured into ethyl acetate and water, the organic phase was separated off and the solvents were stripped off. The residue was washed with a little methanol;
Yield: 290 mg (81%)
$R_f$ (III, 5:1): m/e=0.29
MS (EI): m/e=356 [M$^+$]

Example 12
(3aS*,6aS*)-6a-Naphthalen-2-ylmethyl-hexahydro-cyclopenta[c]furan-1-one

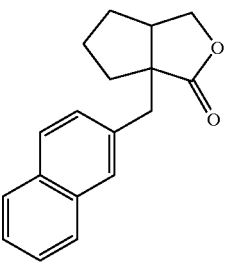

A mixture of the compound from Example 11 (200 mg, 0.56 mmol) and Raney nickel (cat.) in ethanol (75 ml) was heated under reflux for 14 h. The mixture was filtered (kieselguhr) and the solvent was stripped off;
Yield: 120 mg (80%)
$R_f$ (III 5:1)=0.38
MS (ESI): m/e=289 [M+Na$^+$]

Example 13
(3aS*,6aS*)-6a-Naphthalen-2-ylhexahydro-cyclopenta[c]furan-1,5-dione-5-5-oxime

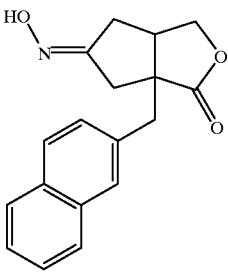

A solution of the compound from Example 10 (280 mg, 1.0 mmol), hydroxylamine hydrochloride (348 mg, 5.0 mmol) and 1,4-diazabicyclooctane (DABCO, 123 mg, 1.1 mmol) in methanol (5 ml) was stirred at room temperature for 20 h. The solvent was stripped off, the residue was stirred with water and the product was filtered off;
Yield: 266.5 mg (90%)
$R_f$ (III, 1:1)=0.22
MS (ESI): m/e=296 [M+H$^+$]

Example 14
(3aS*,6aS*)-5,5-Difluoro-6a-naphthalen-2-yl-hexahydro-cyclopenta[c]furan-1-one

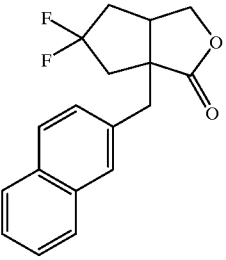

At 0° C., diethylaminosulphur trifluoride (403 mg, 2.5 mmol) was added to a solution of the compound from Example 10 (280 mg, 1.0 mmol) in toluene/dichloromethane (1:1, 20 ml) and the reaction mixture was stirred at room temperature for 20 h. The reaction mixture was mixed with methanol and poured into water, and the resulting precipitate was filtered off and purified by MPLC;
Yield: 150 mg (50%)
$R_f$ (III, 5:1)=0.22
MS (ESI): m/e=303 [M+H$^+$]

Example 15 and Example 16
(3aS*,5S*,6aS*)-5-Amino-6a-naphthalen-2-ylmethyl-hexahydrocyclopenta[c]furan-1-one hydrochloride and (3aS*,5*R,6aS*)-5-amino-6a-naphthalen-2-ylmethyl-hexahydrocyclopenta[c]furan-1-one hydrochloride

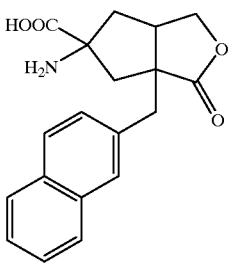

1.) The compound from Example 10 (216 mg, 0.77 mmol), potassium cyanide (100 mg, 1.54 mmol), ammonium carbonate (370 mg, 3.85 mmol) in dimethylformamide/water (10 ml, 1:1) was stirred at 80° C. in a closed vessel for 20 h. The reaction mixture was poured into water (100 ml) and the resulting precipitate was filtered off with suction and washed with water;
Yield: 220 mg (81%) of hydantoin;
$R_f$ (III, 20:1)=0.33 and 0.41
2.) Hydantoin (219 mg. 0.625 mmol), bis-tert-butyloxylcarbonyl (BOC$_2$O, 680 mg, 3.12 mmol), triethylamine (87 μl, 0.6 mmol) and dimethylaminopyridine (DMAP, 15 mg, 0.012 mmol) in DME (5 ml) was stirred at room temperature for 6 h. The reaction mixture was poured into diethyl ether and water (buffer pH=2), the org.

phase was washed with sat. NaHCO$_3$ solution and dried (MgSO$_4$), the solvents were stripped off and the residue was purified by MPLC;

Yield: 300 mg (87%)

R$_f$=0.43 (III) 2:1) of BOC-protected hydantoin

3.) BOC-protected hydantoin (86 mg, 0.156 mmol), sodium hydroxide (62 m, 1.56 mol) in THF/water (2 ml, 1:1) was stirred at room temperature for 20 h. The reaction mixture was adjusted to pH=8, diluted with water and extracted with ethyl acetate (2×), the aqueous phase was adjusted to pH=1 using 1 N Hcl and the water was stripped off. The residue was suspended in methanol and filtered (3×). The combined filtrates were concentrated and the residue was purified by HPLC.

Example 15

(diastereomer A) Yield 15 mg (26%), R$_f$ (V)=0.23

Example 16

(diastereomer B) Yield 7 mg (12%), R$_f$ (V)=0.07

Example 17 to Example 21

3aS*,5RS*,6aS*)-5-Hydroxymethyl-6a-Naphthalen-2-ylmethyl-hexahydro-cyclopenta[c]furan-1-one

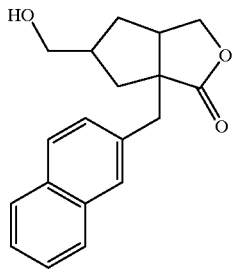

At 0° C., a solution of borane-dimethyl sulphide complex (10 M in CH$_2$Cl$_2$, 31 μl, 0.33 mmol) was added to a solution of the compound from Example 9A (278 mg, 1.0 mmol) in THF (6 ml), and the reaction mixture was stirred at 0° C. for a further 30 min and at room temperature for 3 h. Ethanol (2 ml), 1% NaOH solution (1.6 ml) and 30% H$_2$O$_2$ solution (0.2 ml) were then added, and the mixture was heated under reflux for 1 h. The mixture was poured into ethyl acetate and buffer solution (pH=4), the aqueous phase was extracted with ethyl acetate, the extract was dried (MgSO$_4$) and the solvents were stripped off. The residue was purified by MPLC;

Yield: 180 mg (61%, diastereomer mixture)

MS (ESI): m/e=319 [M+Na$^+$]

The enantiomers (Example 18, 19, 20 and 21) were isolated by HPLC (Daicel Chiral Chiralpak AD, heptane/ethanol 87:13).

Example 18:
(Fraction 1)

Example 19
(Fraction 2)

Example 20
(Fraction 3)

Example 21
(Fraction 4)

Example 22 and Example 23

(3aS*,5R*,6aS*)-5-Hydroxy-6a-naphthalen-2-ylmethyl-hexahydro-cyclopenta[c]furan-1-one and (3aS*,5S*,6aS*-5-hydroxy-6a-naphthalen-2-ylmethyl-hexahydrocyclopenta[c]furan-1-one

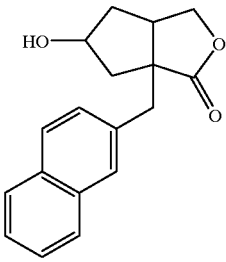

A solution of the compound from Example 10 (1.69 g, 6.04 mmol) in THF (70 ml) was, at 0° C., admixed with a solution of borane-dimethyl sulphide (10 M in THF, 0.187 ml, 1.87 mmol), and the reaction mixture was stirred at room temperature for 20 h. The mixture is poured into ethyl acetate and water, the org. phase is concentrated and the residue is purified by MPLC;

Example 22

Yield: 0.150 g (8%, diastereomer A)

R$_f$ (II, 50:1)=0.23

MS (ESI): m/e=305 [M+Na$^+$]

Example 23

Yield: 0.92 g (54%, diastereomer B)

R$_f$ (II, 50:1)=0.18

MS (ESI): m/e=305 [M+Na$^+$]

Example 24

(3aS*,5RS*,6aS*)-5-Methoxy-6a-naphthalen-2-ylmethyl-hexahydro-cyclopenta[c]furan-1-one

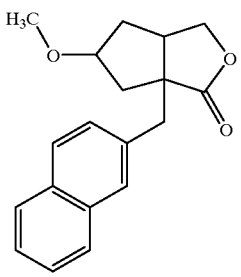

A solution of the compound from Example 22 (diastereomer A, 250 mg, 0.089 mmol) in DMF (1 ml) was admixed with sodium hydride (60% in paraffin oil, 5.3 mg, 0.106 mmol), stirred at room temperature for 1 h, admixed with iodomethane (6.6 μl, 0.133 mmol) and stirred at room temperature for 20 h. For work-up, the mixture is admixed with 1 N HCl solution and ether, the organic phase is separated off, the solvents are stripped off and the residue is purified by flash chromatography;

Yield: 9.3 mg (35%)

R$_f$ (III, 2:1)=0.35

MS (ESI): m/e=297 [M+H$^+$]

The compounds listed in the table below were prepared analogously to Example 24.

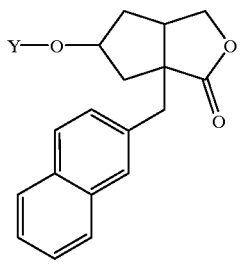

| Ex. No. | Y | Starting material Ex. No. | Yield [%] | $R_f$ | MS |
|---|---|---|---|---|---|
| 25 | benzyl (CH₂-phenyl) | 22 and 23 | 33 | 0.66 (I, 50:1) | 373 [M+H⁺] |
| 26 | H₃C-CH₂-CH₂- | 22 | 47 | 0.448 (III, 2:1) | 311 [M + H⁺] |
| 27 | CH₂=CH-CH₂- | 22 | 82 | 0.50 (III, 2:1) | 323 [M + H⁺] |
| 28 | cyclopropyl-CH₂- | 22 | 65 | 0.50 (III, 2:1) | 337 [M + H⁺] |
| 29 | 4-tBu-phenyl-CH₂- | 22 | 88 | 0.62 (III, 2:1) | 429 [M + H⁺] |
| 30 | H₃C-CH₂- | 23 | 18 | 0.26 (III, 2:1) | 297 [M + H⁺] |
| 31 | H₃C-CH₂-CH₂- | 23 | 26 | 0.42 (III, 2:1) | 311 [M + H⁺] |
| 32 | CH₂=CH-CH₂- | 23 | 46 | 0.46 (III, 2:1) | 323 [M + H⁺] |
| 33 | cyclopropyl-CH₂- | 23 | 33 | 0.50 (III, 2:1) | 337 [M + H⁺] |
| 34 | benzyl | 23 | 51 | 0.75 (III, 2:1) | 373 [M + H⁺] |

Example 35 and Example 36

(3aS*,5R*,6aS*)-5-Methyl-6a-naphthalen-2-ylmethyl-hexahydro-cyclopenta[c]furan-1-1one and (3aS*,5S*, 6aS*)-5-methyl-6a-naphthalen-2-ylmethyl-hexahydro-cyclopenta[c]furan-1-1one

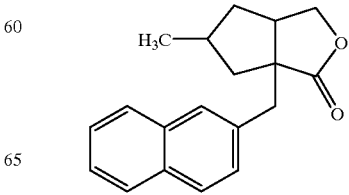

At room temperature, a mixture of the compound from Example 9A (105 mg, 0.38 mmol) and Lindlar catalyst (100 mg) in THF (15 ml) was stirred under hydrogen (1 atm.) for 48 h. The mixture was filtered, the solvents were stripped off and the residue was then purified by HPLC;

Example 35

Yield: 29 mg (27%, diastereomer A)

$R_f$ (II, 10:1)=0.21

MS (ESI): m/e=281 [M+H$^+$]

Example 36

Yield: 9 mg (9%, diastereomer B)

$R_f$ (II, 10:1)=0.21

MS (ESI): m/e=281 [M+H$^+$]

Example 37

(3a"S*,5"RS*,6a"S*)-(6a-naphthalen-2-ylmethylhexahydrocyclopenta[c]]furan-1-on-5-yl)methanesulphonate (Example 37)

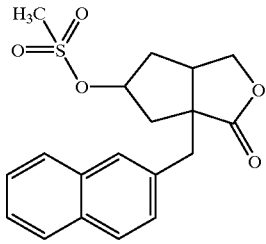

At 0° C. methanesulphonyl chloride was added to a solution of the compound form Example 19 and 20 (diastereomer mixture, 87 mg, 0.31 mmol) and triethylamine 107 μl, 0.77 mmol) in dichloromethane (5 ml), and the reaction mixture was stirred at room temperature for 20 h. The mixture was diluted with dichloromethane, washed with buffer solution (pH=2) and dried (Na$_2$SO$_4$), and the solvents were stripped off under reduced pressure;

Yield: 104 mg (94%, diastereomer mixture)

$R_f$ (III, 1:1)=0.29 and 0.35

Example 38 and Example 39 cis-exo-6-Ethoxycarbonyl-1-(2-naphthylmethyl)-3-oxabicyclo[3.1.0]hexan-2-one (Example 38) and cis-endo-6-ethoxycarbonyl-1-(2-naphthylmethyl)-3-oxa-bicyclo[3.1.0]hexan-2-one (Example 39)

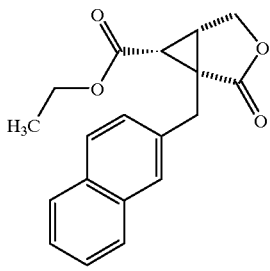

-continued

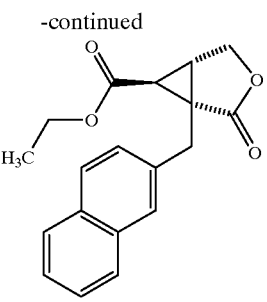

Under argon, ethyl dimethylsulphuranylidene-acetate (593 mg, 4 mmol) in 4 ml of toluene is added dropwise over a period of 5 min to a boiling solution of 3-(2-naphthylmethyl)-5H-furan-2-one (449 mg, 2 mmol) in 2 ml of dry benzene. The mixture is heated under reflux for another 14 h. The solvent is then evaporated and the residue is purified by column chromatography (mobile phase: cyclohexane:ethyl acetate 3:1). Fraction 1 exo-form, racemic, fraction II endo-form, racemic.

Yield: 200 mg (32.2%).

Beispiel 38 exo $R_f$ (III, 1:1)=0.43

MS (CI): m/e=311 [M+H$^+$]

Example 39 endo $R_f$ (III, 1:1)=0.26

MS (CI): m/e=311 [M+H$^+$]

Example 40 cis-6-Methoxycarbonyl-1-(2-naphthylmethyl)-3-oxabicyclo[3.1.0]hexan-2-one

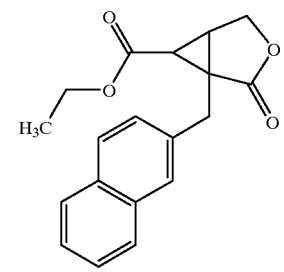

Under argon, methyl dimethylsulphuranylidene-acetate (537 mg, 4 mmol) in 4 ml of toluene is added dropwise over a period of 5 min to a boiling solution of 3-(2-naphthylmethyl)-5H-furan-2-one (450 mg, 2 mmol) in 2 ml of dry toluene. The batch is heated under reflux for another 14 h. The solvent is then evaporated and the residue is purified by column chromatography.

$R_f$ (VII)=0.57

MS (CI)=279 [M+H$^+$]

Example 41
cis-1-Benzyl-8-oxabicyclo[4.3.0]nonan-9-one

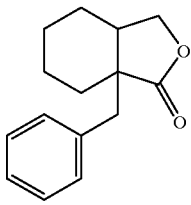

Under argon, a solution of diisopropylamine (3.85 ml, 27.5 mmol) in 20 ml of dry THF is cooled to 0° C. and slowly admixed with butyllithium (11 ml, 27.5 mmol, 2.5M in hexane). With ice-cooling. This solution is stirred for 15 min and then cooled to −78° C. and a solution of cis-8-oxabicyclo[4.3.0]nonan-9-one (3.5 g, 25 mmol) in 10 ml of THF is added dropwise. The mixture is stirred at −78° C. for another 30 min and then mixed with benzyl bromide (3.27 ml, 27 mmol). The mixture is then slowly warmed to room temperature and stirred for another 16 h. The solvent is removed and the residue is taken up in 20 ml of dichloromethane and washed 2× with in each case 20 ml of 2 M HCl. The organic phase is dried over magnesium sulphate, filtered and concentrated. The residue is purified by column chromatography (mobile phase: cyclohexane:ethyl acetate 10:1).

Yield: 2.2 g (38.2%).

$R_f$ (VI)=0.48

MS (CI): m/e=231 [M+H$^+$]

The compounds listed in the table below were prepared analogously to Example 41:

| Ex. No. | Structure | Starting material Ex. No. | Yield (%) | $R_f$ | MS [M + H$^+$] |
|---|---|---|---|---|---|
| 42 | 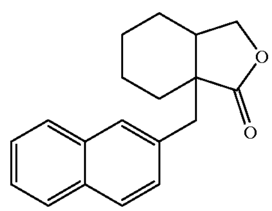 | 1A | 36 | 0.48 (III, 3:1) | 281 |
| 43 | 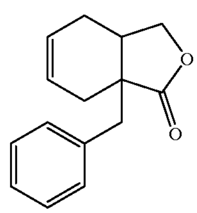 | 2A | 60 | 0.50 (III, 3:1) | 229 |
| 44 | 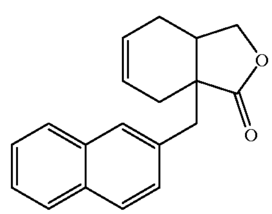 | 2A | 49 | 0.45 (III, 3:1) | 279 |
| 45 | 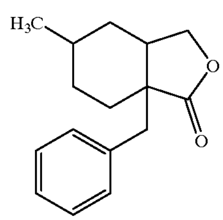 | 3A | 74 | 0.62 (III, 3:1) | 245 |

-continued
| Ex. No. | Structure | Starting material Ex. No. | Yield (%) | $R_f$ | MS [M + H⁺] |
|---|---|---|---|---|---|
| 46 | 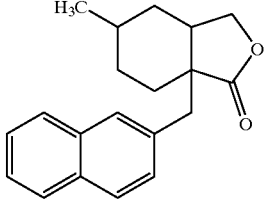 | 3A | 24 | 0.48 (III, 3:1) | 295 |
| 47 | 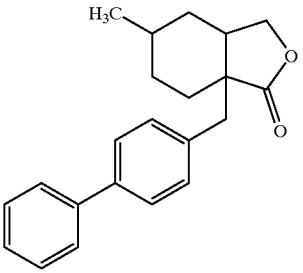 | 3A | 16 | 0.50 (III, 3:1) | 321 |
| 48 | 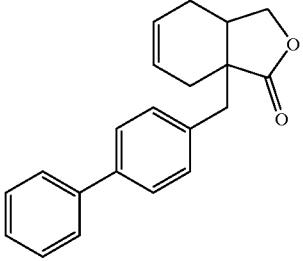 | 2A | 39 | 0.44 (III, 10:1) | 305 |
| 49 | 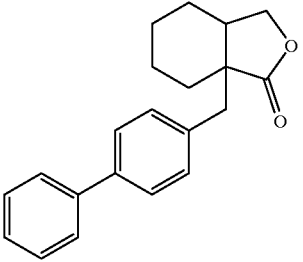 | 1A | 59 | 0.45 (III, 3:1) | 307 |
| 50 | 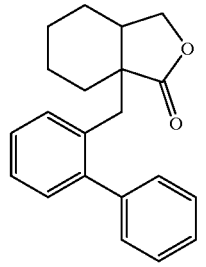 | 1A | 16 | 0.33 (III, 3:1) | 307 |

-continued

| Ex. No. | Structure | Starting material Ex. No. | Yield (%) | $R_f$ | MS [M + H$^+$] |
|---|---|---|---|---|---|
| 51 | 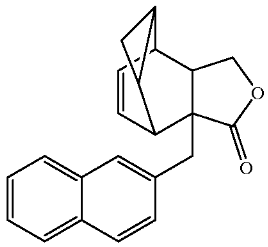 | 6A | 4 | 0.62 (III, 1:1) | 317 |
| 52 | 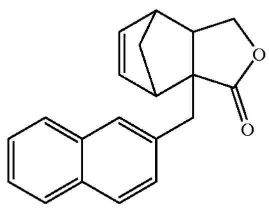 | 4A | 2 | 0.43 (III, 1:1) | 291 |
| 53 | 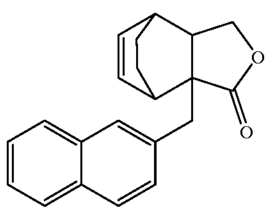 | 5A | 19 | 0.46 (III, 1:1) | 305 |

Example 54

(3aR*,5aS*)-5a-(Naphth-2-ylmethyl)-tetrahydro-cyclobuta(b)furan-1-one

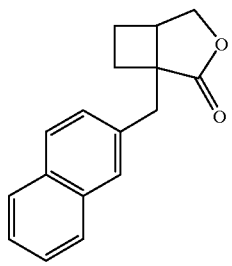

The crude monoester and 0.14 g (1.38 mmol) of triethylamine were dissolved in 10 ml of THF and then, at −15° C., admixed with 0.14 g (1.3 mmol) of ethyl chloroformate. The mixture was stirred at room temperature for one hour and then filtered and the filtrate was concentrated and taken up in 10 ml of methanol. The mixture was admixed with 0.12 g (2 mmol) of sodium borohydride and stirred overnight at room temperature. For work-up, the mixture was admixed with ammonium chloride solution and extracted three times with ethyl acetate, and the combined extracts were dried over sodium sulphate and then concentrated. The mixture was separated chromatographically over silica gel (mobile phase: petroleum ether/ethyl acetate). This gave two main fractions:

| | |
|---|---|
| 1$^{st}$. fraction: | (3aR*,5aS*)-3a-(Naphth-2-ylmethyl)-tetrahydro-cyclobuta(b)furan-2-one |
| 2$^{nd}$. fraction: | n-Butyl 1-(naphth-2-ylmethyl)-2-(hydroxymethyl)-cyclobutane carboxylate. |

The second fraction was, in a mixture of 2.5 ml of 6 n hydrochloric acid and 2.5 ml of dioxane, heated at 60° C. for 2 h. The mixture was then concentrated and dried under high vacuum. This gives 17 mg (73%) of a colourless oil.

$^1$H-NMR (200 Mhz; CDCl$_3$) δ [ppm]: 1.9 (br m; 1H), 2.3 (br m; 3H), 3.0 (d+dd; 2H), 3.32 (d; 1H), 3.53 (dd; 1H), 3.92 (d; 1H), 7.28 (dd; 1H), 7.47 (m; 2H), 7.65 (s; 1H), 7.73–7.82 (m; 3H).

What is claimed is:
1. Compounds of the general formula (I)

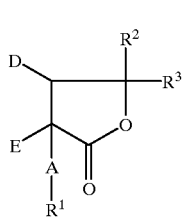

in which
A represents radicals of the formulae —CH$_2$—, —CO—, —CR$^4$(OH)— or —(CH$_2$)$_a$—CHR$^5$—, in which
a represents a number 0, 1, 2, 3 or 4,
$R^4$ represents hydrogen or $(C_1–C_6)$-alkyl and
$R^5$ represents phenyl, or
represents $(C_2–C_8)$-alkanediyl, $(C_2–C_6)$-alkenediyl or $(C_2–C_6)$ alkinediyl,
$R^1$ represents hydrogen, $(C_3–C_6)$-cycloalkyl or represents a 5- to 6-membered heterocycle which may contain up to 3 heteroatoms from the group consisting of S, O and N and/or a radical of the formula —$NR^6$,
in which
$R^6$ represents hydrogen or methyl, or
represents a 5- to 6-membered benzo-fused heterocycle which may contain up to 2 heteroatoms from the group consisting of S, O and N and/or a radical of the formula —$NR^7$, and which may be attached both via the phenyl ring and via the heterocycle, in which
$R^7$ has the meaning of $R^6$ given above and is identical to or different from this meaning, or
represents radicals of the formulae

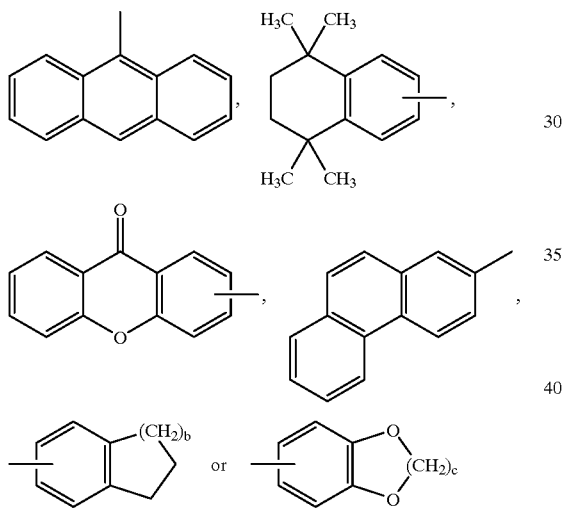

in which
b and c are identical or different and represent a number 1 or 2, or
represents $(C_6–C_{10})$-aryl,
where all of the ring systems listed above are optionally mono- to polysubstituted by identical or different substituents selected from the group consisting of halogen, cyano, nitro, trifluoromethyl, hydroxyl, $(C_1–C_6)$-alkoxy and $(C_3–C_6)$-cycloalkyl, phenyl, phenoxy, benzyloxy and a 5- to 6-membered aromatic heterocycle having up to 3 hetero-atoms from the group consisting of S, N and/or O, which for their part may be substituted up to three times by identical or different substituents from the group consisting of cyano and halogen,
and/or are substituted by $(C_1–C_6)$-alkyl and $(C_2–C_6)$-alkylene, which for their part may be substituted by halogen, $(C_6–C_{10})$-aryl or by radicals of the formulae —$SR^8$, —$OR^9$ or —$NR^{10}R^{11}$ or

in which
$R^8$ represents $(C_1–C_6)$-alkyl or phenyl,
$R^9$ represents hydrogen or $(C_1–C_6)$-alkyl, and
$R^{10}$ and $R^{11}$ are identical or different and represent hydrogen, phenyl or $(C_1–C_6)$-alkyl, which is optionally substituted by phenyl, which for its part may be mono- to polysubstituted by identical or different substituents from the group consisting of halogen, nitro, hydroxyl and $(C_1–C_6)$-alkoxy, or
$R^{10}$ and $R^{11}$ together with the nitrogen atom form a radical of the formula

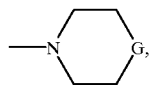

in which
G represents an oxygen atom, a —$CH_2$— group or a radical of the formula —$NR^{12}$—,
in which
$R^{12}$ represents hydrogen, phenyl, benzyl, $(C_1–C_6)$-alkyl, $(C_1–C_6)$-alkoxy-carbonyl or a 5- to 6-membered aromatic hetero-cycle having up to 3 heteroatoms from the group consisting of S, N and/or O,
and/or are substituted by groups of the formulae —$CO_2$—$R^{13}$, —$NR^{14}R^{15}$, —$NR^{16}CO$—$R^{17}$, —$NR^{18}CO_2$—$R^{19}$ and —$CO$—$NR^{20}R^{21}$, in which
$R^{13}$ represents hydrogen, or represents $(C_1–C_9)$-alkyl or $(C_2–C_6)$-alkenyl, which for their part may be substituted by radicals of the formulae

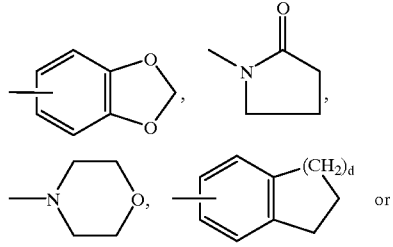

$(C_6–C_{10})$-aryl or by a 5- to 7-membered aromatic heterocycle having up to 3 heteroatoms from the group consisting of S, N and/or O,
in which
d represents a number 1 or 2, or
represents $(C_6–C_{10})$-aryl, which is optionally substituted by phenyl, which for its part may be substituted by cyano or halogen,
$R^{14}$ and $R^{15}$ are identical or different and represent hydrogen, $(C_3–C_6)$-cycloalkyl, phenyl or $(C_1–C_6)$-alkyl, which is optionally substituted by $(C_3–C_6)$-cycloalkyl or phenyl, which for its part may be mono- to polysubstituted by identical or different substituents from the group consisting of halogen, hydroxyl or $(C_1–C_6)$-alkoxy,
$R^{16}$ represents hydrogen or $(C_1–C_6)$-alkyl,
$R^{17}$ represents hydrogen, adamantyl, $(C_3–C_8)$-cycloalkyl, $(C_2–C_6)$-alkenyl or $(C_1–C_{12})$-alkyl which is optionally substituted by adamantyl, $(C_3-C_6)$-cycloalkyl, $(C_6-C_{10})$-aryl, phenoxy or a 5- to 6-membered aromatic heterocycle having up to 3 hetero-atoms from the group consisting of S, N and/or O, where aryl and the heterocycle for their part may be mono- to polysubstituted by identical or different substituents from the group consisting of $(C_1-C_6)$-alkyl, $(C_1-C_6)$-alkoxy, hydroxyl, nitro or halogen, and/or alkyl is optionally substituted by a radical of the formula

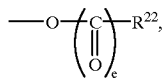

in which
e represents a number 0 or 1 and
$R^{22}$ represents $(C_1-C_6)$-alkyl or $(C_6-C_{10})$-aryl, which is optionally mono- to polysubstituted by identical or different substituents from the group consisting of halogen, nitro, hydroxyl and $(C_1-C_6)$-alkoxy, or
represents $(C_6-C_{10})$-aryl or a 5- to 6-membered aromatic heterocycle having up to 3 heteroatoms from the group consisting of S, N and/or O, which for their part may optionally be mono- to polysubstituted by identical or different substituents from the group consisting of $(C_1-C_6)$-alkoxy, $(C_1-C_6)$-alkyl, hydroxyl, nitro and halogen, or
represents a radical of the formula

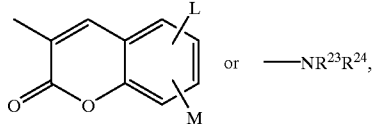

in which
L and M are identical or different and represent hydrogen or halogen,
$R^{23}$ and $R^{24}$ have the meaning of $R^{10}$ and $R^{11}$ given above and are identical to or different from this meaning,
$R^{18}$ has the meaning of $R^{16}$ given above and is identical to or different from this meaning,
$R^{19}$ represents $(C_3-C_8)$-cycloalkyl, or represents $(C_1-C_8)$-alkyl or $(C_2-C_8)$-alkenyl, which for their part are optionally substituted by substituents, selected from the group consisting of halogen, phenyl, hydroxyl, morpholinyl, $(C_3-C_8)$-cycloalkyl and by a group of the formula $-SiR^{25}R^{26}R^{27}$
in which
$R^{25}$, $R^{26}$ and $R^{27}$ are identical or different and represent $(C_1-C_6)$-alkyl,
$R^{20}$ and $R^{21}$ are identical or different and represent hydrogen, adamantyl, $(C_3-C_8)$-cycloalkyl, phenyl, phenoxy-substituted phenyl or a 5- to 6-membered, aromatic heterocycle having up to 3 heteroatoms from the group consisting of S, N and/or O, or
represent $(C_2-C_8)$-alkenyl, $(C_1-C_{12})$-alkyl or $(C_2-C_6)$-alkinyl, which are optionally substituted by hydroxyl, $(C_3-C_6)$-cycloalkyl, $(C_1-C_6)$-alkoxy, halogen, hydroxyl, trifluoromethyl, phenyl or by a 5- to 6-membered aromatic heterocycle having up to 3 heteroatoms from the group consisting of S, N and/or O, where the ring systems are optionally substituted up to 2 times by identical or different substituents from the group consisting of $(C_1-C_6)$-alkoxy, $(C_1-C_6)$-alkoxycarbonyl, halogen, phenoxy, hydroxyl and $(C_1-C_6)$-alkyl, and/or the alkyl listed under $R^{20}/R^{21}$ is optionally substituted by radicals of the formulae

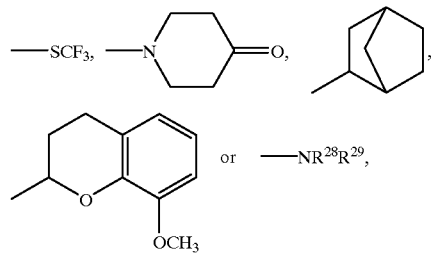

in which
$R^{28}$ and $R^{29}$ are identical or different and represent hydrogen or $(C_1-C_6)$-alkyl, or or
represents a radical of the formula

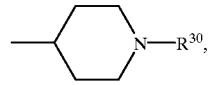

in which
$R^{30}$ has the meaning of $R^{12}$ given above and is identical to or different from this meaning, or
$R^{20}$ and $R^{21}$ together with the nitrogen atom form a radical of the formula

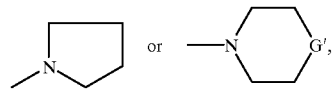

in which
G' has the meaning of G given above and is identical to or different from this meaning,
$R^2$ and $R^3$ are identical or different and represent hydrogen or $(C_1-C_6)$-alkyl, and
D and E together represent radicals of the formulae

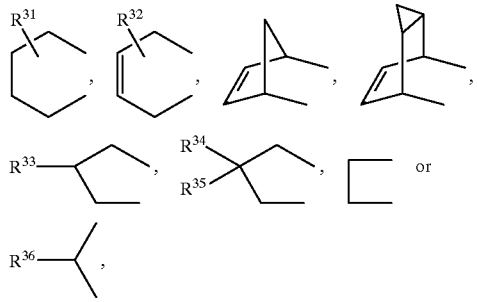

in which
$R^{31}$ and $R^{32}$ are identical or different represent hydrogen or $(C_1-C_6)$-alkyl,
$R^{33}$ represents hydrogen, hydroxyl, $(C_1-C_6)$-alkoxy, $(C_1-C_6)$-alkoxycarbonyl, carboxyl or $(C_1-C_6)$-alkyl, which is optionally substituted by hydroxyl, carboxyl or $(C_1-C_6)$-alkoxycarbonyl, or represents a radical of the formula $-OR^{37}$,
in which
$R^{37}$ represents $(C_1-C_6)$-alkenyl or $(C_1-C_6)$-alkyl, which is optionally substituted by $(C_3-C_8)$-cycloalkyl or $(C_6-C_{10})$-aryl, which for its part is substituted by halogen, nitro, trifluoromethyl or $(C_1-C_6)$-alkyl, or represents a radical of the formula $-SO_2R^{38}$,
in which
$R^{38}$ represents $(C_6-C_{10})$-aryl or $(C_1-C_6)$-alkyl,
$R^{34}$ and $R^{35}$ are identical or different and represent halogen, hydroxyl, carboxyl, $(C_1-C_6)$-acyloxy or amino, or represent $(C_1-C_6)$-alkyl, which is optionally substituted by hydroxyl or $(C_1-C_6)$-acyloxy, or
$R^{34}$ and $R^{35}$ to(ether with the adjacent ring carbon atom form a radical of the formula

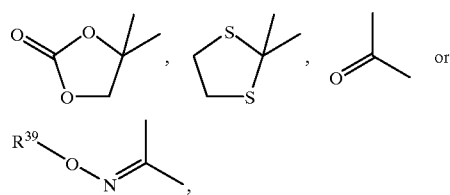

in which
$R^{39}$ represents hydrogen or $(C_1-C_4)$-alkyl, and
$R^{36}$ represents $(C_1-C_6)$-alkoxycarbonyl, or represents $(C_1-C_6)$-alkyl, which is optionally substituted up to 2 times by identical or different substituents from the group consisting of hydroxyl, $(C_1-C_6)$-alkoxy and $(C_1-C_6)$-alkoxycarbonyl, and their pharmaceutically acceptable salts.

2. Compounds of the formula (I) according to claim 1, in which

A represents radicals of the formulae $-CH_2-$, $-CO-$, $-CR^4(OH)-$ or $-(CH_2)_a-CHR^5-$,
in which
a represents a number 0, 1, 2 or 3,
$R^4$ represents hydrogen or $(C_1-C_4)$-alkyl, and
$R^5$ represents phenyl, or
represents $(C_2-C_6)$-alkanediyl, $(C_2-C_4)$-alkenediyl or $(C_2-C_4)$-alkinediyl, R represents hydrogen, cyclopropyl, cyclopentyl or cyclohexyl, or represents benzofuranyl, benzothiophenyl, benzimidazolyl, thienyl, furyl, quinazolyl, quinoxalinyl or quinolyl, or represents radicals of the formulae

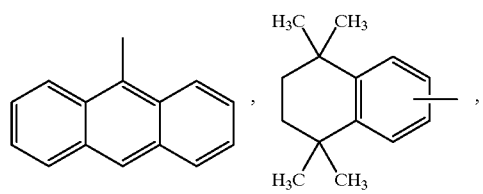

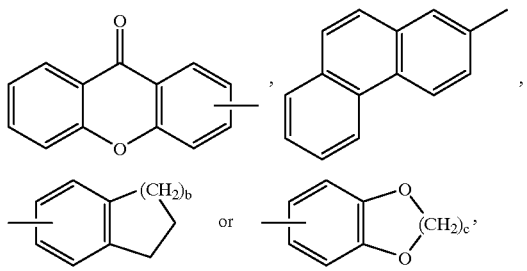

in which
b and c are identical or different and represent a number 1 or 2, or
represents phenyl or naphthyl,
where all of the ring systems listed above may optionally be mono- to polysubstituted by identical or different substituents selected from the group consisting of fluorine, chlorine, bromine, iodine, cyano, nitro, trifluoromethyl, hydroxyl or $(C_1-C_5)$-alkoxy, cyclopropyl, cyclopentyl, cyclohexyl, phenyl, phenoxy, pyridyl, pyrimidyl, pyridazinyl, thienyl, furyl or benzyloxy, which for their part may be substituted up to three times by identical or different substituents from the group consisting of cyano, fluorine, chlorine, bromine and iodine,
and/or are substituted by $(C_1-C_5)$-alkyl and $(C_2-C_4)$-alkenyl, which for their part may be substituted by fluorine, chlorine, bromine, iodine, phenyl, naphthyl or by radicals of the formula $-SR^8$, $-OR^9$ or $-NR^{10}R^{11}$ or

in which
$R^8$ represents $(C_1-C_4)$-alkyl or phenyl,
$R^9$ represents hydrogen or $(C_1-C_4)$-alkyl, and
$R^{10}$ and $R^{11}$ are identical or different and represent hydrogen, phenyl or $(C_1-C_4)$-alkyl, which is optionally substituted by phenyl, which for its part may be mono- to polysubstituted by identical or different substituents from the group consisting of fluorine, chlorine, bromine, nitro, hydroxyl and $(C_1-C_4)$-alkoxy, or
$R^{10}$ and $R^{11}$ together with the nitrogen atom form a radical of the formula

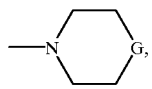

in which
G represents an oxygen atom, a $-CH_2-$ group or a radical of the formula $-NR^{12}-$,
in which
$R^{12}$ represents hydrogen, phenyl, benzyl, $(C_1-C_4)$-alkyl, $(C_1-C_4)$-alkoxycarbonyl, pyridyl, pyrimidyl, pyridazinyl or furyl,
and/or are substituted by groups of the formulae $-CO_2-R^{13}$, $-NR^{14}R^{15}$, $-NR^{16}CO-R^{17}$, $-NR^{18}CO_2-R^{19}$ and $-CO-NR^{20}R^{21}$, in which $R^{13}$ represents hydrogen, or represents $(C_1-C_8)$-alkyl or $(C_2-C_5)$-alkenyl, which for their part may be substituted by radicals of the formulae

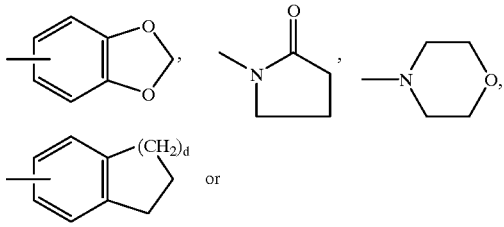

phenyl, naphthyl, pyridyl, thienyl or furyl, in which d represents a number 1 or 2, or represents phenyl or naphthyl, which are optionally substituted by phenyl, which for its part may be substituted by cyano, fluorine, chorine or bromine, $R^{14}$ and $R^{15}$ are identical or different and represent hydrogen, cyclopropyl, cyclopentyl, cyclohexyl, phenyl or $(C_1-C_5)$-alkyl, which is optionally substituted by cyclopropyl, cyclopentyl, cyclohexyl or phenyl, which for its part may be mono- to polysubstituted by identical or different substituents from the group consisting of fluorine, chlorine, bromine, hydroxyl or $(C_1-C_4)$-alkoxy, $R^{16}$ represents hydrogen or $(C_1-C_3)$-alkyl, $R^{17}$ represents hydrogen, adamantyl, cyclopropyl, cyclopentyl or cyclohexyl, or represents $(C_2-C_4)$-alkenyl or $(C_1-C_{10})$-alkyl, which is optionally substituted by adamantyl, cyclopropyl, cyclopentyl, cyclohexyl, phenyl, phenoxy naphthyl, pyridyl, thienyl or furyl, where the ring systems for their part may be mono- to polysubstituted by identical or different substituents from the group consisting of $(C_1-C_4)$-alkyl, $(C_1-C_4)$-alkoxy, hydroxyl, nitro, fluorine, chlorine and bromine, and/or alkyl is optionally substituted by a radical of the formula

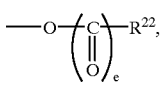

in which e represents a number 0 or 1 and $R^{22}$ represents $(C_1-C_4)$-alkyl, phenyl or naphthyl, which are optionally mono- to polysubstituted by identical or different substituents from the group consisting of fluorine, chlorine, bromine, nitro, hydroxyl and $(C_1-C_4)$-alkoxy, or represents phenyl, naphthyl, thienyl, furyl or pyridyl, which for their part may optionally be mono- to polysubstituted by identical or different substituents from the group consisting of $(C_1-C_4)$-alkoxy, $(C_1-C_4)$-alkyl, hydroxyl, nitro, fluorine, chlorine and bromine, or represents a radical of the formula

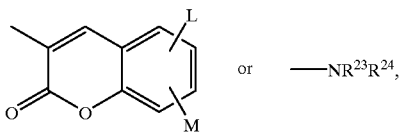

in which

L and M are identical or different and represent hydrogen, fluorine, chlorine or bromine, $R^{23}$ and $R^{24}$ have the meaning of $R^{10}$ and $R^{11}$ given above and are identical to or different from this meaning, $R^{18}$ has the meaning of $R^{16}$ given above and is identical to or different from this meaning, $R^{19}$ represents cyclopropyl, cyclopentyl or cyclohexyl, or represents $(C_1-C_7)$-alkyl or $(C_2-C_6)$-alkenyl, which for their part are optionally substituted by substituents selected from the group consisting of fluorine, chlorine, bromine, phenyl, hydroxyl, morpholinyl, cyclopropyl, cyclopentyl, cyclohexyl and by a group of the formula $-SiR^{25}R^{26}R^{27}$, in which $R^{25}$, $R^{26}$ and $R^{27}$ are identical or different and represent $(C_1-C_4)$-alkyl, $R^{20}$ and $R^{21}$ are identical or different and represent hydrogen, adamantyl, cyclopropyl, cyclopentyl, cyclohexyl, phenyl, phenoxy-substituted phenyl, pyridyl, furyl, thienyl, thiazolyl or pyrryl, or represent $(C_2-C_6)$-alkenyl, $(C_1-C_{10})$-alkyl or $(C_3-C_6)$-alkinyl, which are optionally substituted by hydroxyl, cyclopropyl, cyclopentyl, cyclohexyl, $(C_1-C_5)$-alkoxy, $(C_1-C_6)$-alkoxycarbonyl, fluorine, chlorine, bromine, hydroxyl, trifluoromethyl, phenyl, pyridyl, furyl, thienyl or pyrryl, where the ring systems are optionally substituted up to 2 times by identical or different substituents from the group consisting of $(C_1-C_4)$-alkoxy, fluorine, chlorine, bromine, phenoxy, hydroxyl or $(C_1-C_4)$-alkyl, and/or the alkyl listed under $R^{20}/R^{21}$ is optionally substituted by radicals of the formula

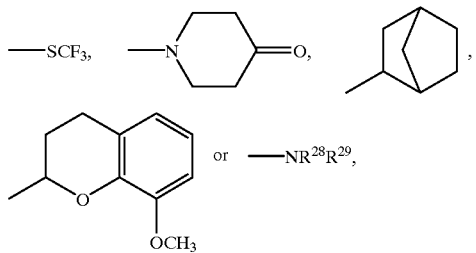

in which $R^{28}$ and $R^{29}$ are identical or different and represent hydrogen or $(C_1-C_4)$-alkyl, or represent a radical of the formula

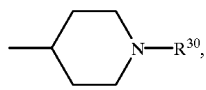

in which $R^{30}$ has the meaning of $R^{12}$ given above and is identical to or different from this meaning, or $R^{20}$ and $R^{21}$ together with the nitrogen atom form a radical of the formula

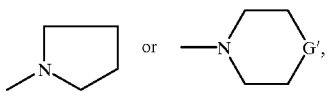

in which

G' has the meaning of G given above and is identical to or different from this meaning, $R^2$ and $R^3$ are identical or different and represent hydrogen or $(C_1-C_3)$-alkyl, and D and E together represent radicals of the formulae

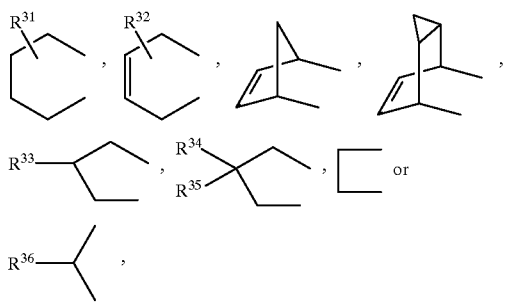

in which $R^{31}$ and $R^{32}$ are identical or different represent hydrogen or $(C_1-C_4)$-alkyl, $R^{33}$ represents hydrogen, hydroxyl, $(C_1-C_4)$-alkoxy, $(C_1-C_4)$-alkoxycarbonyl, carboxyl or $(C_1-C_4)$-alkyl, which is optionally substituted by hydroxyl, carboxyl or $(C_1-C_4)$-alkoxycarbonyl, or represents a radical of the formula —$OR^{37}$, in which $R^{37}$ represents $(C_1-C_4)$-alkenyl or $(C_1-C_4)$-alkyl, which is optionally substituted by cyclopropyl, cyclopentyl, cyclohexyl or phenyl, which for its part may be substituted by trifluoromethyl, fluorine, chlorine, bromine or $(C_1-C_4)$-alkyl, or represents a radical of the formula —$SO_2R^{38}$, in which $R^{38}$ represents phenyl or methyl, $R^{34}$ and $R^{35}$ are identical or different and represent fluorine, chlorine, hydroxyl, carboxyl, $(C_1-C_4)$-acyloxy or amino, or represent $(C_1-C_4)$-alkyl, which is optionally substituted by hydroxyl or $(C_1-C_4)$-acyloxy, or $R^{34}$ and $R^{35}$ together with the adjacent ring carbon atom form a radical of the formula

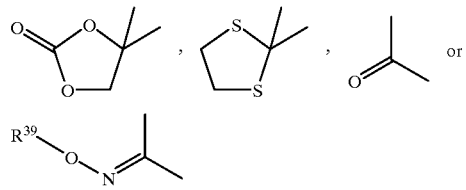

in which $R^{39}$ represents hydrogen or methyl, and $R^{36}$ represents $(C_1-C_4)$-alkoxycarbonyl or $(C_1-C_4)$-alkyl, which is optionally substituted up to 2 times by identical or different substituents from the group consisting of hydroxyl, $(C_1-C_5)$-alkoxy and $(C_1-C_4)$-alkoxycarbonyl, and their pharmaceutically acceptable salts.

3. Compounds of the formula (I) according to claim 1 or 2, in which

A represents radicals of the formulae —$CH_2$—, —CO—, —$CR^4(OH)$— or —$(CH_2)_a$—$CHR^5$—, in which a represents a number 0, 1, 2 or 3, $R^4$ represents hydrogen or $(C_1-C_3)$-alkyl and $R^5$ represents phenyl, or represents $(C_2-C_4)$-alkanediyl, propenediyl or $(C_2-C_3)$-alkinediyl, $R^1$ represents hydrogen, cyclopropyl or cyclohexyl, or represents benzofuranyl, benzothiophenyl, benzimidazolyl, thienyl, quinazolyl or quinoxalinyl, or represents radicals of the formulae

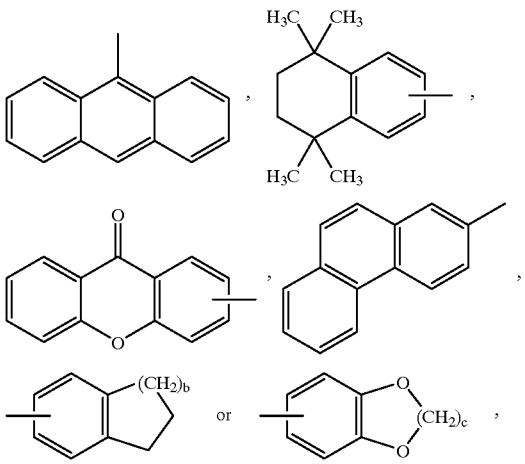

in which b and c are identical or different and represent a number 1 or 2, or represent phenyl or naphthyl, where all of the ring systems listed above are optionally mono- to polysubstituted by identical or different substituents selected from the group consisting of fluorine, chlorine, bromine, iodine, cyano, nitro, trifluoromethyl or $(C_1-C_4)$-alkoxy, cyclohexyl, phenyl, phenoxy, pyridyl, pyrimidyl, pyridazinyl or benzyloxy, which for their part may be substituted up to three times by identical or different substituents from the group consisting of cyano, fluorine, chlorine, bromine and iodine, and/or are substituted by $(C_1-C_4)$-alkyl and $(C_2-C_3)$-alkenyl, which for their part may be substituted by chlorine, bromine, iodine or phenyl or by radicals of the formula —$OR^9$ or —$NR^{10}OR^{11}$ or

in which $R^9$ represents hydrogen or $(C_1-C_3)$-alkyl, and $R^{10}$ and $R^{11}$ are identical or different and represent hydrogen, phenyl or $(C_1-C_3)$-alkyl, which is optionally substituted by phenyl, which for its part may be substituted by chlorine, bromine, hydroxyl or $(C_1-C_3)$-alkoxy, or $R^{10}$ and $R^{11}$ together with the nitrogen atom form a radical of the formula

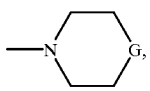

in which

G represents an oxygen atom or a radical of the formula $-NR^{12}$, in which $R^{12}$ represents hydrogen, phenyl, benzyl, $(C_1-C_3)$-alkyl, $(C_1-C_3)$-alkoxycarbonoyl, pyridyl, pyrimidyl, pyridazinyl or furyl, and/or are substituted by groups of the formulae $-CO_2-R^{13}$, $-NR^{14}R^{15}$, $-NR^{16}CO-R^{17}$, $-NR^{18}CO_2-R^{19}$ and $-CO-NR^{20}R^{21}$, in which $R^{13}$ represents hydrogen, or represents $(C_1-C_6)$-alkyl or allyl, which for their part may be substituted by radicals of the formulae

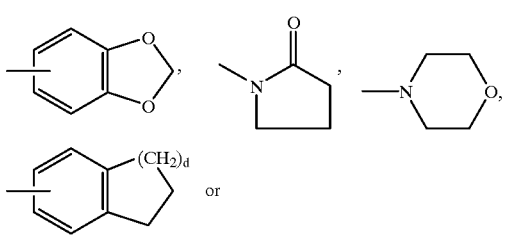

phenyl, naphthyl or pyridyl, in which d represents a number 1 or 2, or represents phenyl, which is optionally substituted by phenyl, which for its part may be substituted by cyano, chlorine or bromine, $R^{14}$ and $R^{15}$ are identical or different and represent hydrogen, cyclohexyl, phenyl or $(C_1-C_4)$-alkyl, which is optionally substituted by cyclopropyl, cyclohexyl or phenyl, which for its part may be mono- to polysubstituted by identical or different substituents from the group consisting of chlorine and $(C_1-C_3)$-alkoxy, $R^{16}$ represents hydrogen, methyl or ethyl, $R^{17}$ represents hydrogen, adamantyl, cyclopentyl or cyclohexyl, or represents $(C_2-C_3)$-alkenyl or $(C_1-C_8)$-alkyl, which is optionally substituted by adamantyl, cyclopropyl, cyclopentyl, cyclohexyl, phenyl, phenoxy, thienyl or furyl, where the ring systems for their part may be mono- to polysubstituted by identical or different substituents from the group consisting of $(C_1-C_3)$-alkyl, $(C_1-C_3)$-alkoxy, hydroxyl, nitro, fluorine, chlorine and bromine, and/or alkyl is optionally substituted by a radical of the formula

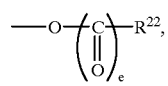

in which e is a number 0 or 1 and $R^{22}$ represents $(C_1-C_3)$-alkyl, phenyl or naphthyl, which are optionally mono- to polysubstituted by identical or different substituents from the group consisting of fluorine, chlorine, bromine, nitro, hydroxyl and $(C_1-C_3)$-alkoxy, or represents phenyl, naphthyl, thienyl or furyl, which for their part may optionally be mono- to polysubstituted by identical or different substituents from the group consisting of $(C_1-C_3)$-alkoxy, $(C_1-C_3)$-alkyl, nitro, fluorine, chlorine and bromine, or represents a radical of the formula

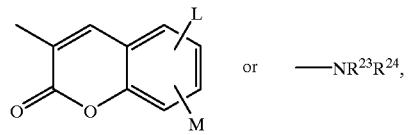

in which

L and M are identical or different and represent hydrogen, fluorine or chlorine, $R^{23}$ and $R^{24}$ have the meaning of $R^{10}$ and $R^{11}$ given above and are identical to or different from this meaning, $R^{18}$ has the meaning of $R^{16}$ given above and is identical to or different from this meaning, $R^{19}$ represents $(C_1-C_4)$-alkyl or $(C_3-C_5)$-alkenyl, which for their part are optionally substituted by substituents selected from the group consisting of chlorine, phenyl, hydroxyl, morpholinyl, cyclopropyl, cyclohexyl and by a group of the formula $-SiR^{25}R^{26}R^{27}$, in which $R^{25}$, $R^{26}$ and $R^{27}$ are identical and represent methyl, $R^{20}$ and $R^{21}$ are identical or different and represent hydrogen, adamantyl, cyclopropyl, cyclopentyl, cyclohexyl, phenyl, phenoxy-substituted phenyl, thiazolyl or pyrryl, or represent $(C_2-C_3)$-alkenyl, $(C_1-C_7)$-alkyl or $(C_3-C_5)$-alkinyl, which are optionally substituted by hydroxyl, cyclopropyl, cyclopentyl, cyclohexyl, $(C_1-C_3)$-alkoxy, hydroxyl, trifluoromethyl, phenyl, pyridyl, furyl, thienyl or pyrryl, where the ring systems are optionally substituted up to 2 times by identical or different substituents from the group consisting of $(C_1-C_3)$-alkoxy, $(C_1-C_6)$-alkoxycarbonyl, fluorine, chlorine, bromine, phenoxy, hydroxyl and $(C_1-C_3)$-alkyl, and/or the alkyl listed under $R^{20}/R^{21}$ is optionally substituted by radicals of the formulae

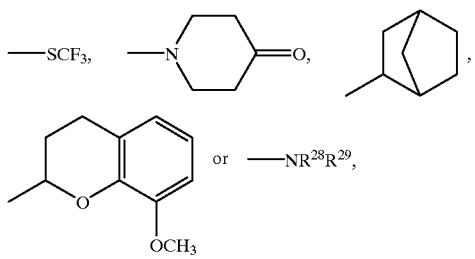

in which $R^{28}$ and $R^{29}$ are identical or different and represent hydrogen or $(C_1-C_3)$-alkyl, or $R^{20}$ or $R^{21}$ represent a radical of the formula

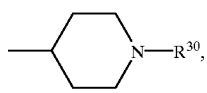

in which $R^{30}$ has the meaning of $R^{12}$ given above and is identical to or different from this meaning, $R^{20}$ and $R^{21}$ together with the nitrogen atom form a radical of the formula

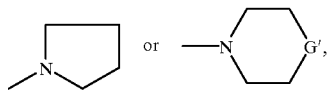

in which

G' has the meaning of G given above and is identical to or different from this meaning, $R^2$ and $R^3$ are identical or different and represent hydrogen or methyl, and D and E together represent radicals of the formulae

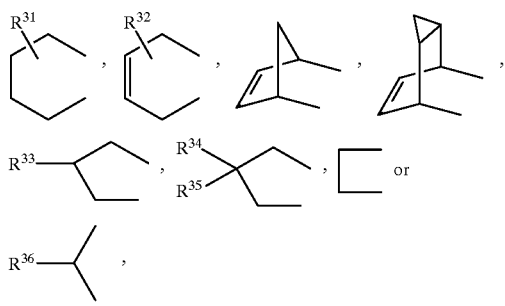

in which $R^{31}$ and $R^{32}$ are identical or different represent hydrogen or $(C_1-C_3)$-alkyl, $R^{33}$ represents hydrogen, hydroxyl, $(C_1-C_3)$-alkoxy, $(C_1-C_3)$-alkoxycarbonyl, carboxyl or $(C_1-C_3)$-alkyl, which is optionally substituted by hydroxyl or $(C_1-C_3)$-alkoxycarboxyl, or represents a radical of the formula $—OR^{37}$, in which $R^{37}$ represents $(C_1-C_3)$-alkenyl or $(C_1-C_3)$-alkyl, which is optionally substituted by cyclopropyl, cyclopentyl, cyclohexyl or phenyl, which for its part may be substituted by trifluoromethyl, fluorine, chlorine, bromine or $(C_1-C_3)$-alkyl, or represents a radical of the formula $—SO_2R^{38}$, in which $R^{38}$ represents methyl, $R^{34}$ and $R^{35}$ are identical or different and represent fluorine, chlorine, hydroxyl, carboxyl, $(C_1-C_3)$-acyloxy or amino, or represent $(C_1-C_3)$-alkyl, which is optionally substituted by hydroxyl or $(C_1-C_3)$-acyloxy, or $R^{34}$ and $R^{35}$ together with the adjacent ring carbon atom form a radical of the formula

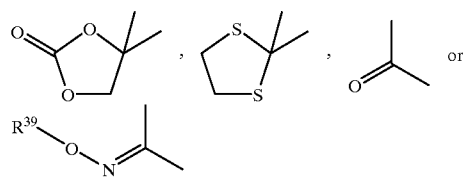

in which $R^{39}$ represents hydrogen or methyl, and $R^{36}$ represents $(C_1-C_3)$-alkoxycarbonyl or $(C_1-C_3)$-alkyl, which is optionally substituted up to 2 times by identical or different substituents from the group consisting of hydroxyl, $(C_1-C_4)$-alkoxy or $(C_1-C_3)$-alkoxycarbonyl, and their pharmaceutically acceptable salts.

4. Compounds of the formula (I) according to claim 1, in which

A represents the $—CH_2—$ group, and $R^1$ represents phenyl, biphenyl or naphthyl.

5. Compounds according to claim 1, selected from the group consisting of:

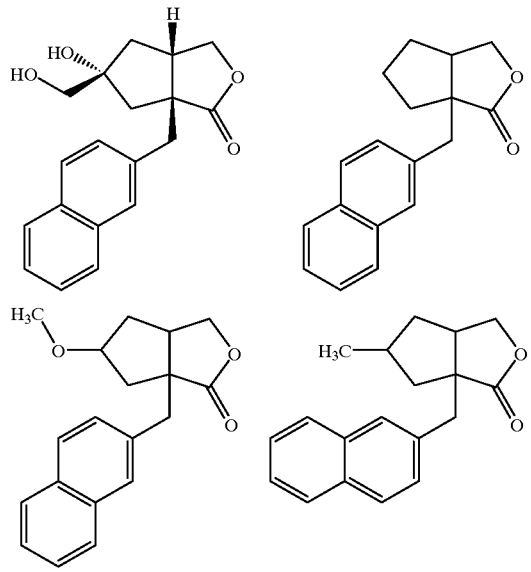

6. Process for preparing compounds of the formula (I) according to claim 1, by reacting compounds of the general formula (II)

(IV)

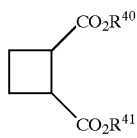

in which

D, E, $R^2$ and $R^3$ are as defined above in claim 1, with compounds of the general formula (III),

T—A—$R^1$ (III)

in which

T represents halogen, and

A and $R^1$ are as defined above in claim 1, in inert solvents and in the presence of a base.

7. Pharmaceutical composition, comprising as an active component at least one compound according to a claim 1 mixed together with at least one pharmaceutically acceptable, essentially non-toxic vehicle or excipient.

8. The process of claim 6, wherein T is bromine.

9. The process of claim 6, further comprising the step of derivatizing the substituent $R^1$.

10. A method of preventing and/or treating a disorder caused by the hyper- or hypofunction of the glutamatergic system, comprising administering to a patient in need thereof an effective amount of a compound according to claim 1.

11. A method of preventing and/or treating cerebral ischaemias, cranial cerebral trauma, states of pain or CNS-mediated spasms, comprising administering to a patient in need thereof an effective amount of a compound according to claim 1.

* * * * *